US006277981B1

(12) United States Patent
Tu et al.

(10) Patent No.: US 6,277,981 B1
(45) Date of Patent: Aug. 21, 2001

(54) METHOD FOR DESIGN AND SELECTION OF EFFICACIOUS ANTISENSE OLIGONUCLEOTIDES

(75) Inventors: Guang-Chou Tu, East Norriton; Yedy Israel, Philadelphia, both of PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/109,663

(22) Filed: Jul. 2, 1998

Related U.S. Application Data
(60) Provisional application No. 60/051,705, filed on Jul. 3, 1997.

(51) Int. Cl.[7] ............... A61K 31/7088; C07H 21/00; C12Q 1/68
(52) U.S. Cl. ............ 536/25.3; 435/6; 435/3.75; 514/44; 536/24.5
(58) Field of Search ............ 435/6, 91.1, 375; 514/44; 536/24.3, 24.31, 24.33, 24.5, 25.3

(56) References Cited

U.S. PATENT DOCUMENTS
5,034,506    7/1991   Summerton et al. .

OTHER PUBLICATIONS

Agrawal et al., 1988, Proc. Natl. Acad. Sci. U.S.A. 86:7790–7794.
Agrawal, 1996, Trends Biotechnol. 14:376–387.
Alahari et al., 1996, Mol. Pharmacol. 50:808–819.
Bautista et al., 1992, Gen. Leukoc. Biol. 51:39–45.
Bennett et al., 1994, J. Immunol. 152:3530–3540.
Bennett et al., 1994, Adv. Pharmacol. 28:1–43.
Bennett et al., 1992, Mol. Pharmacol. 41:1023–1033.
Bennett et al., 1993, J. Liposome Res. 3:85–102.
Bird et al., 1990, Ann. Int. Med. 112:917–920.
Bishop et al., 1996, J. Clin. Oncol. 14:1320–1326.
Cao et al., 1998, Alcoholism Clin. Exp. Res. 22:108a.
Chiang et al., 1991, J. Biol. Chem. 266:18162–18171.
Colige et al., 1993, Biochem. 32:7–11.
Cotter et al., 1994, Oncogene 9:3049–3055.
Crooke, 1993, FEBS J. 7:533–539.
Crooke et al., 1996, Annu. Rev. Pharmacol. Toxicol. 36:107–129.
Dean et al., 1994, J. Biol. Chem. 269:16416–16424.
Dean et al., 1996, Biochem. Soc. Trans. 24:623–629.
Dean et al., 1994, Proc. Natl. Acad. Sci. U.S.A. 91:11762–11766.
Duff et al., 1995, J. Biol. Chem. 270:7161–7166.
Felver et al., 1990, Alcohol. Clin. Exp. Res. 14:255–259.
Fenster et al., 1994, Biochemistry 33:8391–8398.
Gewirtz et al., 1996, Proc. Natl. Acad. Sci. U.S.A. 93:3161–3163.
Giles et al., 1995, Antisense Res. Dev. 5:23–31.
Goodchild et al., 1988, Proc. Natl. Acad. Sci. USA 85:5507–5511.
d'Hellencourt et al., 1996, Biochim. Biophys. Acta 1317:168–174.
Ho et al., 1996, Nucl. Acids Res. 24:1901–1907.
Ho et al., 1998, Nature Biotechnol. 16:59–63.
Johansson et al., 1994, Nucl. Acids Res. 22:4591–4598.
Kamimura et al., 1995, Hepatol. 21:1304–1309.
Khoruts et al., 1991, Hepatol. 13:267–276.
Kramer et al., 1984, Cell 38:299–307.
Laptev et al., 1994, Biochemistry 33:11033–11039.
Lee et al., 1995, Shock 4:1–10.
Lima et al., 1992, Biochem. 31:12055–12061.
Lima, et al., 1997, Biochemistry 36:390–398.
Matteucci et al., 1996, Nature 384(Supp.):20–22.
McClain et al., 1986, Life Sci. 39:1479–1485.
Monia et al., 1996, Nature Med. 2:668–675.
Monia et al., 1992, J. Biol. Chem. 267:19954–19962.
Nedwin et al., 1985, Nucl. Acids Res. 13:6361–6373.
Nielsen et al., 1991, Science 254:1497–1500.
Ojala et al., 1997, Antisense Nucl. Drug Dev. 7:31–38.
Perlaky et al., 1993, Anti–cancer Drug Des. 8:3–14.
Ratmeyer et al., 1994, Biochemistry 33:5298–5304.
Sheron et al., 1991, Clin. Exp. Immunol. 84:449–453.
Shirai et al., 1989, Agric. Biol. Chem. 53:1733–1736.
Stein 1998, Antisense and Nucleic Acid Drug Development 8:129–132.
Stull et al., 1992, Nucl. Acids Res. 20:3501–3508.
Stutz et al., 1997, Mol. Cell. Biol. 17:1759–1767.
Szoka, 1997, Nature Biotechnol. 15:509.
Thierry et al., 1993, Biochem. Biophys. Res. Commun. 190:952–960.
Tu et al., 1995, J. Biol. Chem. 270:28402–28407.
Vernos et al., 1995, Cell 81:117–127.
Wang et al., 1995 Proc. Natl. Acad. Sci. USA 92:3318–3322.
Wickstrom, et al., 1991, In *Prospects for antisense nucleic acid therapy of cancer and AIDS*, Wickstrom, ed., Wiley––Liss, Inc., New York, 7–24.
Yamagami et al., 1996, Blood 87:2878–2884.

*Primary Examiner*—John L. LeGuyader
*Assistant Examiner*—Thomas G. Larson
(74) *Attorney, Agent, or Firm*—Akin, Gump, Strauss, Hauer & Feld, L.L.P.

(57) ABSTRACT

The invention includes methods for predicting whether an antisense oligonucleotide (ASO) will be efficacious for inhibiting expression of a gene. The invention also includes methods of making efficacious ASOs, comprising a 5'-TCCC-3' motif or another chemical entity which is capable of Watson-Crick-type base-pairing with a 5'-GGGA-3' motif in an RNA molecule such as a primary transcript or an mRNA. The invention further includes ASOs which are useful for inhibiting expression of one of tumor necrosis factor-a in a mammal. Methods of treating an animal comprising a disease or disorder which is characterized by the presence of an RNA molecule in a cell of the animal are also included.

13 Claims, 6 Drawing Sheets

```
   1 gaattccggg tgatttcact cccggctgtc caggcttgtc ctgctacccc acccagcctt
  61 tcctgaggcc tcaagcctgc caccaagccc ccagctcctt ctccccgcag gacccaaaca
 121 caggcctcag gactcaacac agcttttccc tccaacccgt tttctctccc tcaacggact
 181 cagctttctg aagcccctcc cagttctagt tctatctttt tcctgcatcc tgtctggaag
 241 ttagaaggaa acagaccaca gacctggtcc ccaaaagaaa tggaggcaat aggttttgag
 301 gggcatgGGG Acggggttca gcctccaggg tcctacacac aaatcagtca gtggcccaga
 361 agaccccct cggaatcgga gcaGGGAgga tgGGGAgtgt gaggggtatc cttgatgctt
 421 gtgtgtcccc aactttccaa atccccgccc ccgcgatgga gaagaaaccg agacagaagg
 481 tgcaggcc actaccgctt cctccagatg agctcatggg tttctccacc aaggaagttt
 541 tccgctggtt gaatgattct ttccccgccc tcctctcgcc ccaGGGAcat ataaaggcag
 601 ttgttggcac accagccag cagacgctcc ctcagcaagg acagcagagg accagctaag
 661 aGGGAgagaa gcaactacag accccctg aaaacaaccc tcagacgcca catcccctga
 721 caagctgcca ggcaggtct cttcctctca catactgacc cacggcttca ccctctctcc
 781 cctgaaaagg acaccatgag cactgaaagc atgatccGGG Acgtggagct ggcgaggag
 841 gcgctcccca agaagacagg ggggcccag ggctccaggc ggtgcttgtt cctcagcctc
 901 ttctccttcc tgatcgtggc aggcgcacc acgctcttct gcctgctgca ctttggagtg
 961 atcggccccc agaGGGAaga ggtgagtgcc tgccagcct tcatccactc tcccacccaa
1021 gGGGAaatga gagacgcaag agaGGGAgag agatGGGAtg ggtgaaagat gtgcgctgat
1081 aGGGAGGGAt gagagagag aaaacatgga gaaagacgGG GAtgcagaaa gagatgtggc
1141 aagagatgGG GAagagagag agagaaagat gatgtctggc acatggaagg
1201 tgctcactaa gtgtgtatgg agtgatgaa tgaatgaatg aatgaacaag cagatatata
1261 aataagatat ggagacagat gtggggtgtg agaagagaga tgGGGAaga aacaagtgat
1321 atgaataaag atggtgagac agaaagagcG GGAaatatga cagctaagga gagagatggg
1381 ggagataaag agagaagaag ataggggtgtc tggcacacag aagacactca GGGAaagagc
1441 tgttgaatgc tggaaggtga atacacagat gaatggagag agaaaaccag acacctcagg
1501 gctaagagcg caggccagac aggcagccag ctgttcctcc tttaagggtg actccctcga
1561 tgttaaccat tctccttctc cccaacagtt cccaGGGAc ctctctctaa tcagcccctct
```

Fig. 4A

```
1621  ggcccaggca  gtcagtaagt  gtctccaaac  ctctttccta  attctgggtt  tgggttttggg
1681  ggtagggtta  gtaccggtat  ggaagcagtg  gGGGAaattt  aaagtttggg  tcttgGGGA
1741  ggatggatgg  agtgaaagt  aggggggtat  tttctaggaa  gtttaaggt   ctcagctttt
1801  tctttctct   ctcctcttca  ggatcatctt  ctcgaaccc   gagtgacaag  cctgtagccc
1861  atgttgtagg  taagagctct  gaggatgtgt  cttggaactt  ggagggctag  gatttgGGGA
1921  ttgaagcccg  gctgatggta  ggcagaactt  ggagacaatg  tgagaaggac  tcgctgagct
1981  caaGGGAagg  gtggaggaac  agcacaggcc  ttagtGGGAt  actcagaacg  tcatggccag
2041  gtGGGAtgtG  GGAtgacaga  cagagaggac  aggaaccgga  tgtgggtgg   gcagagctcg
2101  agggccagga  tgtggagagt  gaaccgacat  ggccacactg  actctcctct  ccctctctcc
2161  ctccctccag  caaaccctca  agctgagggg  cagctccagt  ggctgaaccg  ccggccaat
2221  gccctcctgg  ccaatgcgt   ggagctgaga  gataaccagc  tggtggtgcc  atcagagggc
2281  ctgtacctca  tctactccca  ggtcctcttc  aagggccaag  gctgcccctc  cacccatgtg
2341  ctcctcaccc  acaccatcag  ccgcatcgcc  gtctcctacc  agaccaaggt  caacctcctc
2401  tctgccatca  agagccctg   acccagagg   gggctgaggc  caagccctgg
2461  tatgagccca  tctatctGGG  ccagaGGGAg  cagctggaga  agggtgaccg  actcagcgct
2521  gagatcaatc  ggcccgacta  tctcgacttt  gccgagtctg  ggcagttcta  ctttGGGAtc
2581  attgccctgt  gaggaggacg  aacatccaac  cttcccaaac  gcctcccctg  cccaatccc
2641  tttattaccc  cctccttcag  acaccctcaa  ttagaacttt  aagcaacaag  gaattggggg
2701  cttagggtcg  gaaccaagc   tgtgtggcct  gcacagtgaa  gtgctggcaa  accaccactt  cgaaacctgg
2761  gattcaggaa  tgtgtggcct  gcacagtgaa  gcctacagct  ttgatccctg  ccactaagaa  ttcaaactgg
2821  ggcctccaga  actcactggg  gcctacagct  cagaatgctg  caggacttga  acatctgaa   tctggagacc
2881  aGGGAgcctt  tggttctggc  cagaatgctg  cttcctctct  ccagatgttt  gaagacttca  cctagaaatt
2941  gacacaagtg  gaccttagc   ctccccatgg  agccagctcc  ccagatgctg  gtttgcactt  gtgattattt
3001  gagccagcc   ctcccatgg   ttatttacag  ctctatttat  atgaatgtat  ttatttGGGA  gaccgggta
3061  attatttatt  tattatttat  ttatttacag  atgaatgtat                ttatttGGGA  gaccgggta
3121  tcctgGGGA   cccaatgtag  gagctgcctt  ggctcagaca  tgttttccgt  gaaaacggag
3181  ctgaacaata  ggctgttccc  atgtagcccc  ctgcctctg   tgccttcttt  tgattatgtt
```

Fig. 4B

```
3241  ttttaaaata  tttatctgat  taagttgtct  aaacaatgct  gatttggtga  ccaactgtca
3301  ctcattgctg  agcctctgct  ccccagGGGA  gttgtgtctg  taatcgccct  actattcagt
3361  ggcgagaaat  aaagtttgct  tagaaaagaa  acatggtctc  cttcttggaa  ttaattctgc
3421  atctgcctct  tcttgtgggt  GGGAagaagc  tccctaagtc  ctctctccac  aggcttttaag
3481  atccctcgga  cccagtccca  tccttagact  cctagggccc  tggagaccct  acataaacaa
3541  agcccaacag  aatattcccc  atcccccagg  aaacaagagc  ctgaacctaa  ttacctctcc
3601  ctcagggcat  GGGAattttcc  aactctGGGA  attc
```

Fig. 4C

SEQUENCE LISTING

```
<160> NUMBER OF SEQ ID NOS: 81

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:  Candidate
      TNF(alpha) ASO

<400> SEQUENCE: 1
cctcgctgag ttctgccggc t                                                 21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:  Candidate
```

TNF(alpha) ASO

<400> SEQUENCE: 2
ccgtgctcat ggtgtcctt c                                         21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 3
gatcatgctt tccgtgctca t                                        21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 4
ggcactcacc tcctccttgt t                                        21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 5
acacttactg agtgtgaggg t                                        21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 6
aaacttacct acgacgtggg c                                        21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 7
gtcgcctcac agagcaatga c                                        21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

```
<400> SEQUENCE: 8
agtgagttcc gaaagcccat t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 9
ggcatcgaca ttcggggatc c                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 10
tgatccactc cccctccac t                                               21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 11
cagccttgtg agccagaggc a                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 12
ggaggcctga gacatcttca g                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 13
agggaaggaa ggaaggaagg g                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO
```

<400> SEQUENCE: 14
ctgagggagg gaaggaagga a                                           21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  Candidate
      TNF(alpha) ASO

<400> SEQUENCE: 15
ggttccgtaa ggaaggctgg                                             20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:  Candidate
      TNF(alpha) ASO

<400> SEQUENCE: 16
aataataaat aataaataaa t                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:  Candidate
      TNF(alpha) ASO

<400> SEQUENCE: 17
ttcccaacgc tgggtcctcc a                                           21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:  Candidate
      TNF(alpha) ASO

<400> SEQUENCE: 18
cccccgatcc actcaggcat c                                           21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:  Candidate
      TNF(alpha) ASO

<400> SEQUENCE: 19
actcccccga tccactcagg c                                           21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:  Candidate
      TNF(alpha) ASO

<400> SEQUENCE: 20
tccactcccc cgatccactc a                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 21
ccctccactc ccccgatcca c                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 22 ccccctcca ctcccccgat c                                               21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 23
actcccccct ccactccccc g                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 24
tccactcccc cctccactcc c                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 25
tgatccactc cccctccac t                                               21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 26

-continued

```
gcctgatcca ctcccccctc c                                              21
```

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 27

```
gcagcctgat ccactccccc c                                              21
```

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 28

```
gaggcagcct gatccactcc c                                              21
```

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 29

```
agtggagggg ggagtggatc a                                              21
```

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 30

```
ccctcactgc tacctcacct c                                              21
```

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 31

```
actccccct ccactcccc                                                  19
```

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 32

```
tccactcccc cgatccac                                                  18
```

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 33
tgatccactc cccct                                                   16

<210> SEQ ID NO 34
<211> LENGTH: 3634
<212> TYPE: DNA
<213> ORGANISM: Homo sapiens
<220> FEATURE:
<223> OTHER INFORMATION: TNF(alpha) cDNA

<400> SEQUENCE: 34
gaattccggg tgatttcact cccggctgtc caggcttgtc ctgctacccc acccagcctt    60
tcctgaggcc tcaagcctgc caccaagccc ccagctcctt ctccccgcag gacccaaaca   120
caggcctcag gactcaacac agcttttccc tccaacccgt tttctctccc tcaacggact   180
cagctttctg aagcccctcc cagttctagt tctatctttt tcctgcatcc tgtctggaag   240
ttagaaggaa acagaccaca gacctggtcc ccaaaagaaa tggaggcaat aggttttgag   300
gggcatgggg acgggttca gcctccaggg tcctacacac aaatcagtca gtggcccaga   360
agacccccct cggaatcgga gcagggagga tggggagtgt gaggggtatc cttgatgctt   420
gtgtgtcccc aactttccaa atccccgccc cgcgatgga gaagaaaccg agacagaagg   480
tgcagggccc actaccgctt cctccagatg agctcatggg tttctccacc aaggaagttt   540
tccgctggtt gaatgattct ttccccgccc tcctctcgcc ccaggacat ataaaggcag   600 ttgttggcac acccagccag cagacgctcc ctcagcaagg acagcagagg accagctaag   660
agggagagaa gcaactacag acccccctg aaaacaaccc tcagacgcca catccctga   720 caagctgcca ggcaggttct cttcctctca catactgacc cacggcttca ccctctctcc   780
cctggaaagg acaccatgag cactgaaagc atgatccggg acgtggagct ggccgaggag   840
gcgctcccca agaagacagg ggggcccag gctccaggc ggtgcttgtt cctcagcctc   900
ttctccttcc tgatcgtggc aggcgccacc acgctcttct gcctgctgca ctttggagtg   960
atcggccccc agagggaaga ggtgagtgcc tggccagcct tcatccactc tcccacccaa  1020
ggggaaatga gagacgcaag agaggagag agatgggatg ggtgaaagat gtgcgctgat  1080
agggagggat gagagagaaa aaacatgga gaaagacggg gatgcagaaa gagatgtggc  1140
aagagatggg gaagagagag agagaaagat ggagagacag gatgtctggc acatggaagg  1200
tgctcactaa gtgtgtatgg agtgaatgaa tgaatgaatg aatgaacaag cagatatata  1260
aataagatat ggagacagat gtgggtgtg agagagaga tggggaagaa acaagtgat   1320 atgaataaag atggtgagac agaaagagcg ggaaatatga cagctaagga gagagatggg  1380
ggagataagg agagaagaag ataggtgtc tggcacacag aagacactca gggaaagagc  1440
tgttgaatgc tggaaggtga atacacagat gaatggagag agaaaccag acacctcagg  1500 gctaagagcg caggccagac aggcagccag ctgttcctcc tttaagggtg actccctcga  1560
tgttaaccat tctccttctc cccaacagtt ccccaggac ctctctctaa tcagccctct  1620
ggcccaggca gtcagtaagt gtctccaaac ctctttccta attctgggtt tgggtttggg  1680

```
ggtagggtta gtaccggtat ggaagcagtg ggggaaattt aaagttttgg tcttgggga      1740 ggatggatgg aggtgaaagt agggggggtat tttctaggaa gtttaagggt ctcagctttt   1800
tcttttctct ctcctcttca ggatcatctt ctcgaacccc gagtgacaag cctgtagccc    1860
atgttgtagg taagagctct gaggatgtgt cttggaactt ggagggctag gatttgggga   1920
ttgaagcccg gctgatggta ggcagaactt ggagacaatg tgagaaggac tcgctgagct   1980
caagggaagg gtggaggaac agcacaggcc ttagtgggat actcagaacg tcatggccag    2040
gtgggatgtg ggatgacaga cagagaggac aggaaccgga tgtggggtgg gcagagctcg   2100
agggccagga tgtggagagt gaaccgacat ggccacactg actctcctct ccctctctcc   2160
ctccctccag caaaccctca agctgagggg cagctccagt ggctgaaccg ccgggccaat   2220
gccctcctgg ccaatggcgt ggagctgaga gataaccagc tggtggtgcc atcagagggc   2280
ctgtacctca tctactccca ggtcctcttc aagggccaag gctgcccctc cacccatgtg    2340
ctcctcaccc acaccatcag ccgcatcgcc gtctcctacc agaccaaggt caacctcctc    2400
tctgccatca agagcccctg ccagagggag accccagagg gggctgaggc caagccctgg   2460
tatgagccca tctatctggg aggggtcttc cagctggaga agggtgaccg actcagcgct   2520
gagatcaatc ggcccgacta tctcgacttt gccgagtctg ggcaggtcta ctttgggatc    2580
attgccctgt gaggaggacg aacatccaac cttcccaaac gcctcccctg ccccaatccc    2640
tttattaccc cctccttcag acaccctcaa cctcttctgg ctcaaaaaga gaattggggg   2700
cttagggtcg gaacccaagc ttagaacttt aagcaacaag accaccactt cgaaacctgg   2760
gattcaggaa tgtgtggcct gcacagtgaa gtgctggcaa ccactaagaa ttcaaactgg   2820
ggcctccaga actcactggg gcctacagct ttgatccctg acatctggaa tctggagacc    2880
agggagcctt tggttctggc cagaatgctg caggacttga gaagacctca cctagaaatt   2940
gacacaagtg gaccttaggc cttcctctct ccagatgttt ccagacttcc ttgagacacg   3000
gagcccagcc ctccccatgg agccagctcc ctctatttat gtttgcactt gtgattattt    3060
attatttatt tattatttat ttatttacag atgaatgtat ttatttggga gaccggggta    3120 tcctgggggga cccaatgtag gagctgcctt ggctcagaca tgttttccgt gaaaacggag    3180
ctgaacaata ggctgttccc atgtagcccc ctggcctctg tgccttcttt tgattatgtt    3240
ttttaaaata tttatctgat taagttgtct aaacaatgct gatttggtga ccaactgtca   3300
ctcattgctg agcctctgct ccccagggga gttgtgtctg taatcgccct actattcagt    3360
ggcgagaaat aaagtttgct tagaaaagaa acatggtctc cttcttggaa ttaattctgc    3420
atctgcctct tcttgtgggt gggaagaagc tccctaagtc ctctctccac aggctttaag   3480
atccctcgga cccagtccca tccttagact cctagggccc tggagaccct acataaacaa   3540
agcccaacag aatattcccc atcccccagg aaacaagagc ctgaacctaa ttacctctcc   3600
ctcagggcat gggaatttcc aactctggga attc                               3634
```

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Known Effective ASO

<400> SEQUENCE: 35

```
cctgctcccc cctggctcc                                                  19
```

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Known
      Effective ASO

<400> SEQUENCE: 36
cccccaccac ttcccctctc                                                   20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Known
      Effective ASO

<400> SEQUENCE: 37
cccccaccac ttcccctctc a                                                 21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 38
tagacgataa agggtcaga g                                                  21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 39
cagtctggga agctctgagg g                                                 21

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 40
gggatagctg gtagtttag                                                    19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 41
catttctttt ccaagcgaac                                                   20

```
<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 42
aggctcctgt ttccggggag a                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 43
ctggtccctt ggtgtcctcg c                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 44
ttgctgttct ccctcctggc t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 45
ttcttgccct ccctccctac t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 46
cctctttccc ttaccctcct g                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 47
ggtctccctc cccaactctc c                                              21
```

```
<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 48
cttcttccct gttccctgg c                                               21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 49
tatctccctc gtctcccatc t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 50
gtttcccctc catctccctc c                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 51
gaagcctccc cgctctttgc c                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 52
aaagctttaa gtcccccgcc c                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 53
cctattccct ttcctcccaa a                                              21

<210> SEQ ID NO 54
```

```
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 54
cccttaggtt tcccagcaag c                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 55
ctggtctttc cacgtcccat t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 56
gcagccttgt cccttgaaga g                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 57
cttgagctca gctccctcag g                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 58
gctggaagac tcctcccagg t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 59
gctgagcagg tcccccttct c                                              21

<210> SEQ ID NO 60
<211> LENGTH: 21
```

```
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 60
agagccacaa ttccctttct a                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 61
gcctgaagac agcttcccaa c                                              21

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 62
cagtcacggc tcccgtggg                                                 19

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 63
gggaaattcc caggaccagg g                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 64
atttggaatt cccagagtgg g                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Candidate
      TNF(alpha) ASO

<400> SEQUENCE: 65
actttcccag caggtatttg g                                              21

<210> SEQ ID NO 66
<211> LENGTH: 20
<212> TYPE: DNA
```

<213> ORGANISM: Artificial Sequence
<220> FEATURE:
<223> OTHER INFORMATION: Description of Artificial Sequence: Known
      Effective ASO

<400> SEQUENCE: 66
cagccatggt tccccccaac                                          20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Known
      Effective ASO

<400> SEQUENCE: 67
ttccccagat gcacctgttt                                          20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Known
      Effective ASO

<400> SEQUENCE: 68
gacatccctt tcccctcgg                                           20

<210> SEQ ID NO 69
<211> LENGTH: 16
<212> TYPE: DNA
<213> ORGANISM: Artificial Sequence
<220> FEATURE:
<223> OTHER INFORMATION: Description of Artificial Sequence: Known
      Effective ASO

<400> SEQUENCE: 69
gatccccggg taccga                                              16

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Known
      Effective ASO

<400> SEQUENCE: 70
gtcagccatg gtccccccccc                                         20

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Known
      Effective ASO

<400> SEQUENCE: 71
atgccctcat ccttccccccc at                                      22

<210> SEQ ID NO 72
<211> LENGTH: 20
<212> TYPE: DNA
<213> ORGANISM: Artificial Sequence

```
<220> FEATURE:
<223> OTHER INFORMATION: Description of Artificial Sequence:  Known
      Effective ASO

<400> SEQUENCE: 72
gttctcccag cgtgtgccat                                              20

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence:  Known
      Effective ASO

<400> SEQUENCE: 73
aacccttatt tgtgtcccac c                                            21

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:  Known
      Effective ASO

<400> SEQUENCE: 74
gtcccaagag ttgaggag                                                18

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence:  Known
      Effective ASO

<400> SEQUENCE: 75
cacccgcctt ggcctcccac                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:  Known
      Effective ASO

<400> SEQUENCE: 76
tcccgcctgt gacatgcatt                                              20

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence:  Known
      Effective ASO

<400> SEQUENCE: 77
ccatcccgac ctcgcgct                                                18

<210> SEQ ID NO 78
<211> LENGTH: 18
<212> TYPE: DNA
<213> ORGANISM: Artificial Sequence
<220> FEATURE:
```

-continued

```
<223> OTHER INFORMATION: Description of Artificial Sequence:  Known
      Effective ASO

<400> SEQUENCE: 78
ccacgtcccg gatcatgc                                                     18

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence:  Known
      Effective ASO

<400> SEQUENCE: 79
tctgctgtcc ctgtaataaa                                                   20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence:  Known
      Effective ASO

<400> SEQUENCE: 80
aacccagtgc tccctttgct                                                   20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:  Known
      Effective ASO

<400> SEQUENCE: 81
aaaacgtcag ccatggtccc                                                   20
```

METHOD FOR DESIGN AND SELECTION OF EFFICACIOUS ANTISENSE OLIGONUCLEOTIDES

CROSS REFERENCE TO RELATED APPLICATIONS

This application is entitled to priority, pursuant to 35 U.S.C. § 119(e), to U.S. Provisional Application No. 60/051,705, filed July 3, 1997.

STATEMENT REGARDING FEDERALLY SUPPORTED RESEARCH AND DEVELOPMENT

This work was supported in part by a grant from the National Institute on Alcohol Abuse and Alcoholism (NIH/NIAAA Grant No. R01-10967) and the U.S. Government may therefore have certain rights in this invention.

FIELD OF THE INVENTION

The field of the invention is antisense oligonucleotides.

BACKGROUND OF THE INVENTION

Antisense oligonucleotides (hereinafter, "ASO"s) are short, usually synthetic, nucleic acids designed to bind to mRNA or other nucleic acids comprising specific sequences, taking advantage of Watson-Crick-type base pairing. Prior art ASO therapeutic strategies are designed to suppress the expression of specific genes involved in cancer, inflammatory diseases, and viral infections (Crooke et al., 1996, Annu. Rev. Pharmacol. Toxicol. 36:107–129). More than ten ASOs are currently undergoing human clinical trials for the treatment of various diseases (Matteucci et al., 1996, Nature 384(Supp.):20–22; Agrawal, 1996, Trends Biotechnol. 14: 376–387).

Antisense therapy comprising binding of an ASO to mRNA in a cell affected by a disease or disorder has, to date, been a therapeutic strategy wherein it has been difficult to identify efficacious target sites for a given RNA sequence (Gewirtz et al., 1996, Proc. Natl. Acad. Sci. U.S.A. 93:3161–3163). A significant shortcoming of prior art antisense strategies is the inability to accurately predict which ASOs will prove efficacious among a population of potentially efficacious ASOs (Laptev et al., 1994, Biochemistry 33:11033–11039). Because prior art attempts to predict the therapeutic efficacy of ASOs have been largely unsuccessful, selection of ASO sequences for antisense therapy has, prior to the present disclosure, been performed by empirically screening large numbers of potential antisense agents (Bennett et al., 1994, J. Immunol. 152:3530–3540). Using trial-and-error ASO selection strategies of the prior art, a large number of ASOs must be tested in order to discover a few sequences which exhibit significant efficacy as therapeutic ASOs. Prior art strategies require the screening of large numbers of ASOs because any portion of an mRNA molecule can be used to design a complementary ASO.

For example, an mRNA molecule which consists of 2000 nucleotide residues affords 1980 potential target sites for an ASO comprising twenty-one nucleotides which is complementary to twenty-one sequential nucleotide residues of the mRNA molecule. The trial-and-error methods of the prior art ASO selection process therefore recommend the manufacture and assay of at least 30–40 potential ASOs in order to identify likely no more than a few efficacious ASOs. Clearly, a method of designing ASOs which reduces or avoids dependence on trial-and-error selection methods would be of great value by reducing the duration and expense of ASO development efforts.

Investigations have been made by others to determine the effect upon efficacy of designing ASOs complementary to various regions of mRNA molecules. In general, these investigations have concentrated on complementation of an ASO to a discrete region within MRNA molecules. For example, various investigators have determined that efficacious ASOs may be constructed which are complementary:

a) to regions encompassing the 5'-cap site of an mRNA molecule (Ojala et al., 1997, Antisense Nucl. Drug Dev. 7:31–38), b) to regions encompassing the transcription start site (Monia et al., 1992, J. Biol. Chem. 267:19954–19962), c) to regions encompassing the translation initiation codon (Dean et al., 1994, Proc. Natl. Acad. Sci. U.S.A. 91:11762–11766), d) to regions encompassing the translation stop codon (Wang et al., 1995, Proc. Natl. Acad. Sci. USA 92:3318–3322), e) to regions encompassing sites at which mRNA molecules are spliced (Agrawal et al., 1988, Proc. Natl. Acad. Sci. U.S.A. 86:7790–7794; Colige et al., 1993, Biochem. 32:7–11), f) to regions encompassing the 5'-untranslated region of mRNA molecules (Duff et al., 1995, J. Biol. Chem. 270:7161–7166; Yamagami et al., 1996, Blood 87:2878–2884), g) to regions encompassing the 3'-untranslated region of mRNA molecules (Bennett et al., 1994, J. Immunol. 152:3530–3540; Dean et al., 1994, J. Biol. Chem. 269:16146–16424), and h) to regions encompassing the coding region (Laptev et al., 1994, Biochem. 33:11033–11039; Yamagami et al., 1996, Blood 87:2878–2884).

Because efficacious ASOs may, as demonstrated by these investigators, be complementary to any region of an mRNA molecule, the ASO designer is not provided any meaningful guidance by these studies.

Several strategies have been proposed to facilitate and simplify the selection process for efficacious ASOs. One strategy relies upon predictions of the binding energy between an ASO and a complementary sequence in an mRNA molecule. Chiang et al. (1991, J. Biol. Chem. 266:18162–18171) designed ten ASOs complementary to mRNA encoding human ICAM-1 protein with the aid of the computer program, OLIGO. These ten oligonucleotides were designed to maximize the melting temperature ($T_m$) of the oligonucleotide-mRNA complex. However, these investigators discovered that the efficacy of the ASOs as inhibitors of ICAM-1 expression did not correlate directly with either the Tm of the oligonucleotide-mRNA complex or the $\Delta G°_{37}$ (change in free energy upon association/dissociation of the oligonucleotide and the mRNA complex, as assessed at 37° C.). The most potent oligonucleotide (ISIS 1939) identified by these investigators exhibited a $T_m$ value that was lower than those corresponding to the majority of the other oligonucleotides which were tested. Thus, maximization of binding energy between an ASO and a complementary mRNA is not sufficient to ensure therapeutic efficacy of the oligonucleotide.

Stull et al. (1992, Nucl. Acids Res. 20:3501–3508) investigated a systematic approach for predicting appropriate sequences within an mRNA molecule against which complementary ASOs could be constructed, by calculating three thermodynamic indices: (i) a secondary structure score (Sscore), (ii) a duplex score (Dscore); and (iii) a competition score (Cscore), which is the difference between the Dscore and the Sscore. The Sscore estimates the strength of local mRNA secondary structures at the mRNA binding site for the ASO. The Dscore estimates AGformation, the change in Gibbs free energy upon formation of the duplex, of the oligonucleotide-mRNA target sequence duplex. These three indices were compared to the efficacy of ASOs for inhibiting protein expression. It was found that the Dscore was the most consistent predictor of ASO efficacy in four of the five studies (the correlation factor $r^2$ ranged from 0.44 to 0.99 in these four studies). The results of the fifth study could not be predicted by any thermodynamic or physical index.

A second strategy for selecting efficacious ASOs is based upon predicting the secondary structure of mRNA. Wickstrom and colleagues (1991, In *Prospects for antisense nucleic acid therapy of cancer and AIDS*, Wickstrom, ed., Wiley-Liss, Inc., New York, 7–24) attempted to correlate the efficacy of potential ASOs with the secondary structure of the complementary region of the mRNA. It was hypothesized that ASOs would be the most efficacious when they were designed to be complementary to the target sequences within the mRNA molecule which were the least involved in the secondary and tertiary structure of the mRNA molecule. These investigators designed fourteen ASOs which were complementary to the predicted stems, loops, and bulges of human C-myc p65 mRNA. ASOs were designed which were complementary to regions of the mRNA molecule between the 5'-cap site and the translation initiation codon AUG, and included oligonucleotides which were complementary to sequences located within a predicted hairpin sequence which was located immediately 3' to the AUG initiation codon. These investigators discovered that two fragments, one comprising the 5'-cap sequence and the other comprising a sequence located slightly 3' relative to the cap sequence, were better target sequences for ASOs than the sequence spanning the AUG initiation codon, even though the sequence spanning the AUG initiation codon was located at an even weaker bulge and stem area.

Lima et al. (1992, Biochem. 31:12055–12061) designed six ASOs, each of which was complementary to a portion of a 47-nucleotide region that was able to achieve a stable hairpin conformation within an activated Ha-ras gene transcript. These investigators discovered that two of the oligonucleotides which were complementary to the loop portion of the hairpin structure had nearly equal binding affinity for the transcript. In contrast, they observed that oligonucleotides which were complementary to the double-stranded stem portion of the hairpin structure were less tightly bound, having affinity constants that were smaller by a factor of between $10^5$ and $10^6$. These results suggest that mRNA sequences which lie within regions of secondary structure may be undesirable target sequences for designing complementary ASO.

Thierry et al. (1993, Biochem. Biophys. Res. Commun. 190:952–960) compared the efficacy of ASOs which were complementary to either the 5'-end of the coding region of or to a single-stranded loop in the mRNA encoded by the multidrug resistance gene mdr1. The results obtained by these investigators indicate that the oligonucleotides targeted to the single-stranded loop were more efficacious and specific than the oligonucleotides targeted to the 5'-end coding region. However, Laptev et al. (1994, Biochem. 33:11033–11039) obtained results which were not consistent with that suggestion. Laptev et al. concluded that the most efficacious ASOs were those which were complementary to mRNA sequences that were predicted to form clustered double-stranded secondary structures.

Still other investigators presented evidence that the most efficacious ASOs (ISIS 1939 and ISIS 2302) were those which were complementary to regions of human ICAM-1 mRNA, which regions were predicted by computer modeling to form stable stem-loop structures (Chiang et al., 1991, J. Biol. Chem. 266:18162–18171; Bennett et al., 1994, J. Immunol. 152:3530–3540). Oligonucleotides which were complementary to mRNA sequences upstream or downstream from these putative stem-loop structures had significantly less inhibitory activity (Bennett et al., 1994 Adv. Pharmacol. 28:1).

Fenster et al. (1994, Biochemistry 33, 8391–8398) observed that inhibition of gene expression by an ASO was highly dependent upon the position of the mRNA sequence to which the oligonucleotide was complementary. These investigators discovered that the most potent ASOs to effect inhibition of the Rev-response element of the human immunodeficiency virus (HIV) were complementary to mRNA target sites corresponding to the stem-loop V region of the HIV mRNA. This region of the HIV mRNA is known to be important for full and efficient Rev-response element function. ASOs targeted to other, noncritical Rev-response element stem-loops (e.g. SLI and SLIII) were determined by these investigators to be either non-efficacious or 30-fold less efficacious than stem-loop V oligonucleotides for inhibiting Rev-response element function.

Hence, it is clear that the bulk of ASO selection strategies reported in the prior art have been directed to designing ASOs which are complementary to discrete regions within mRNA molecules, rather than to particular sequences within mRNA.

Recently, Ho et al. (1996, Nucl. Acids Res. 24:1901–1907; 1998, Nature Biotechnol. 16:59–63) developed a novel approach to rationally select ASOs. These investigators contacted an mRNA molecule encoding human multidrug resistance-1 protein and an mRNA molecule encoding angiotensin type I receptor protein with a library of chimeric oligonucleotides. Hybridized mRNA was subsequently treated with RNase H, an enzyme which catalyzes the hydrolytic cleavage of only the RNA strand of an RNA-DNA duplex. The RNA fragments which were generated were sequenced to identify regions on the mRNA sequence which were involved in RNA-DNA duplex formation. Using the sequence information, these investigators constructed ASOs which were complementary to these regions and found those particular ASOs to be significantly more efficacious than randomly-selected oligonucleotides for inhibiting human multidrug resistance-1 protein or angiotensin type I receptor protein expression. These results demonstrate that it is feasible to construct improved ASOs by incorporating therein sequences which are complementary to particular nucleotide sequences found in mRNA molecules.

Skilled workers in the art have concluded the therapeutic efficacy of an ASO which is complementary to a particular target sequence within an mRNA molecule has not heretofore been accurately predictable (Gewirtz et al., 1996, Proc. Natl. Acad. Sci. U.S.A. 93:3161–3163). Because efficacious ASOs have been made which are complementary to most or all regions of mRNA molecules, the ASO designer cannot be meaningfully guided by selection of any particular mRNA region. Methods for predicting the efficacy of ASOs by maximization of Tm or AGformation have not consistently yielded correct predictions, and thus are similarly of limited use to the ASO designer. Analyses of the secondary structure of an mRNA do not clearly identify potential ASO-binding sites. Library-based RNaseH degradation studies are laborious and complex. Other skilled workers in the art have recognized that a long-felt, but unmet, need exists for methods of selecting the most potent target sequences within a given mRNA sequence (Szoka, 1997, Nature Biotechnol. 15:509).

In April of 1998, results of a consensus reached at U.S. National Institutes of Health conference on this subject were reported. These results included the conclusions that "[i]t appears that the only way to generate an active oligomer is by brute force" and that "[o]ptimally it is best to screen 30–40 oligos to obtain one species that is maximally active, but this may be impossible because of time and cost considerations" (Stein, 1998, Antisense and Nucleic Acid Drug Development 8: 129–132).

Taken together, the results of these prior art methods for designing an ASO sequence offer little guidance to the ASO designer. The present invention overcomes the shortcomings of prior art ASO design methods by providing a method for designing efficacious ASOs.

SUMMARY OF THE INVENTION

The invention relates to an antisense oligonucleotide for inhibiting expression of a gene which encodes TNF-α in an animal. The oligonucleotide comprises from 12 to 50 nucleotide residues. At least 90% of the nucleotide residues of this oligonucleotide are complementary to a region of an RNA molecule which corresponds to the gene, and the region comprises a GGGA motif. In one embodiment, the oligonucleotide comprises from 14 to 30 nucleotide residues, comprises a TCCC motif, and at least 95% of the nucleotide residues of the oligonucleotide are complementary to the region. In another embodiment, the oligonucleotide comprises from 16 to 21 nucleotide residues, comprises a TCCC motif, and is completely complementary to the region. Preferably, the oligonucleotide has a nucleotide sequence selected from the group consisting of SEQ ID NOs: 19–27, SEQ ID NOs: 31–33, SEQ ID NOs: 44–55, SEQ ID NO: 57, SEQ ID NO: 58, SEQ ID NO: 60, and SEQ ID NO: 61. Also preferably, the animal is a human.

The invention also relates to a method of making an antisense oligonucleotide for inhibiting expression of a gene in an animal. This method comprises identifying an RNA molecule corresponding to the gene, wherein the RNA molecule comprises a GGGA motif; and synthesizing an oligonucleotide complementary to at least a portion of the RNA molecule. The portion comprises the GGGA motif. In one embodiment of this method, at least a portion of the oligonucleotide comprises a randomly-generated sequence. In another embodiment, gene is a human gene. In still another embodiment, the RNA molecule is the primary transcript of the gene.

The invention includes an antisense oligonucleotide made by this method.

The invention further relates to a method of treating an animal afflicted with a disease or disorder characterized by the presence in an affected cell of the animal of an RNA molecule which corresponds to a gene and comprises a region comprising a GGGA motif. This method comprises providing an antisense oligonucleotide which is at least 90% complementary to the region and administering the oligonucleotide to the animal. In one aspect of this method, the antisense oligonucleotide is at least 95% complementary to the region. In a preferred embodiment, the antisense oligonucleotide is completely complementary to the region. In yet another embodiment, the RNA molecule is the primary transcript of the gene. Preferably, the animal is a human and the encodes human TNF-α. In another aspect of this method, at least one linkage between nucleotide residues of the oligonucleotide is a phosphorothioate linkage.

The invention also relates to a method of inhibiting expression of a gene in an animal cell. This method comprises administering to the cell an antisense oligonucleotide which is complementary to a region of an RNA molecule corresponding to the gene, wherein the region comprises a GGGA motif.

The invention includes a method of predicting the efficacy of an antisense oligonucleotide for inhibiting expression of a gene. This method comprises determining whether the antisense oligonucleotide is complementary to a region of an RNA molecule corresponding to the gene, wherein the region comprises a GGGA motif. If so, this is an indication that the antisense oligonucleotide is efficacious for inhibiting expression of the gene.

The invention further relates to a method of separating from a mixture of oligonucleotides an antisense oligonucleotide which is efficacious for inhibiting expression of a gene. This method comprises contacting the mixture with a support linked to an oligonucleotide comprising a GGGA motif, whereby the efficacious antisense oligonucleotide associates with the support, and separating the support from the mixture.

BRIEF DESCRIPTION OF THE DRAWINGS

FIG. 4 is the nucleotide structure of the human TNF-α gene. Nucleotide residues corresponding to GGGA motifs in transcription products encoding TNF-α are indicated with capital letters. Nucleotide residues corresponding to regions of a transcription product which could be used as target sequences for design of efficacious ASO having a length of up to 21 nucleotide residues are underlined.

DETAILED DESCRIPTION

Figure 1:
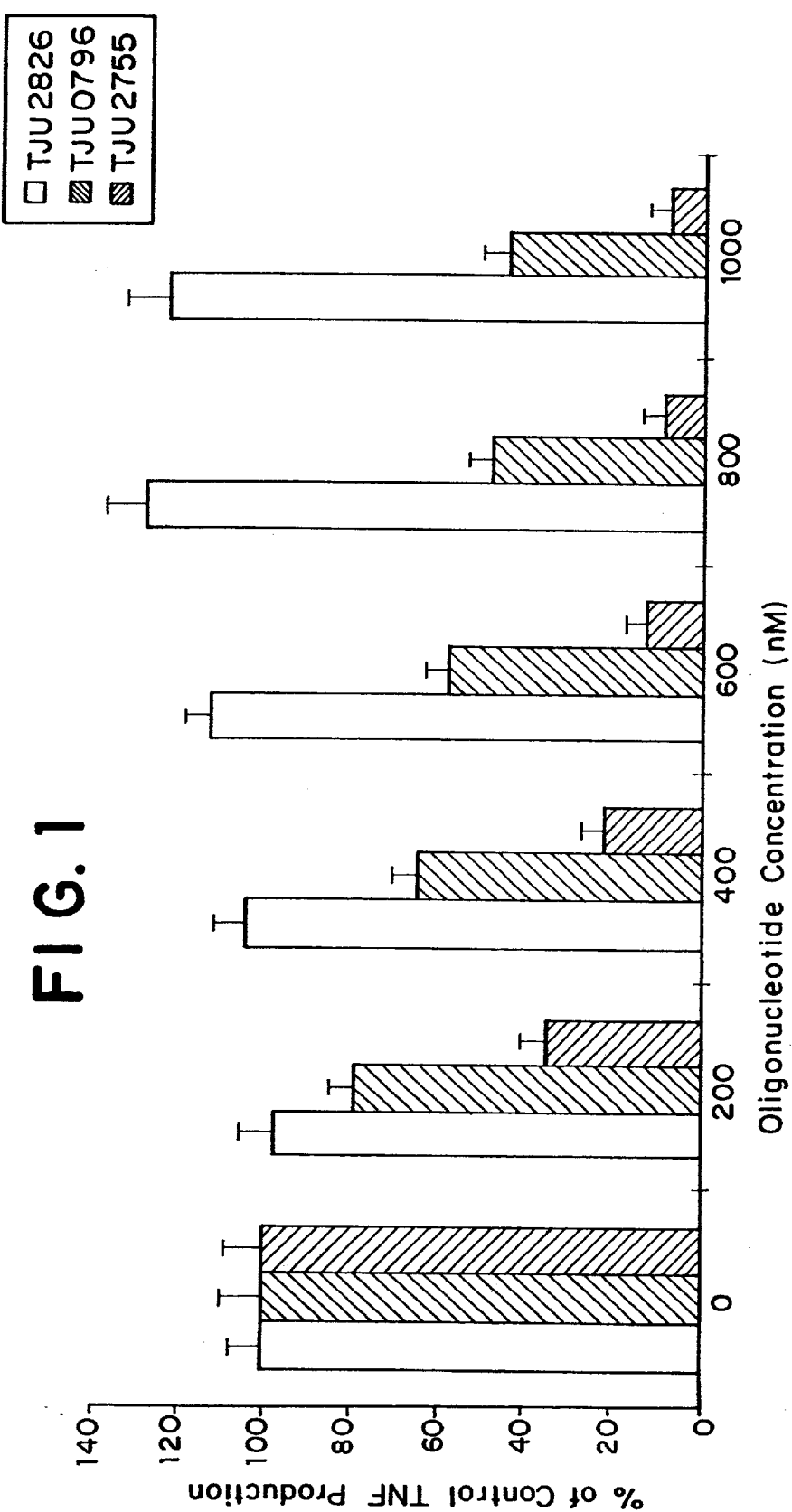
FIG. 1 is a bar graph which depicts the effect of three different ASOs on the expression of TNF-α by cultured Kupffer cells. Data are reported as a percentage of TNF-α protein expression in control cultures which were not treated with an ASO.

The invention relates to the discovery of a method of designing efficacious ASOs for use in antisense nucleic acid methods including, but not limited to, methods of inhibiting gene expression.

This discovery was made during a study wherein a large number of phosphorothioate-modified ASOs, each comprising from nineteen to twenty-one nucleotide residues, were designed to be complementary to various regions of an RNA molecule which encodes rat TNF-α protein. After screening the ASOs for their ability to inhibit expression of TNF-α, it was observed that only an ASO which was complementary to a fragment in the 3'-untranslated region of the mRNA markedly inhibited (i.e. >90% inhibition) the expression of TNF-α protein by cultured rat Kupffer cells. The gene which specifies this mRNA fragment has been reported (GENBANK DDBJ D00475; NCBI Seq. Id. # 220920). The nucleotide sequence of this gene comprises twenty-eight tetranucleotide 5'-GGGA-3' sequences (hereinafter referred to as "GGGA motifs"). Accordingly, ASOs which were complementary to this sequence had nucleotide sequences which comprised at least one copy of the sequence 5'-TCCC-3' (hereinafter referred to as a "TCCC" motif).

A series of ASOs, each comprising between sixteen and twenty-one nucleotide residues, were designed, synthesized, and screened to determine the efficacy thereof for inhibiting expression of TNF-α protein. It was discovered that most ASOs which were complementary to at least one of the twenty-eight TNF-α GGGA motifs (i.e. any ASO having a nucleotide sequence comprising at least one TCCC motif) displayed high inhibitory efficacy.

It was further discovered that the presence of the TCCC motif in an ASO is an indication that the ASO is efficacious for inhibiting protein expression from genes unrelated to TNF-α.

Because the presence of the GGGA motif in an RNA molecule has not previously been identified as a basis for designing efficacious ASOs, the existence of known efficacious ASOs having sequences comprising a TCCC motif was investigated. The results of a comprehensive search indicated that about half of the most efficacious ASOs which have been reported comprise the TCCC motif. Recognition of the significance of the TCCC motif in efficacious ASOs represents a significant advance over the prior art. The presence of the TCCC motif in an ASO complementary to an RNA molecule is an indication that the ASO will inhibit expression of the protein encoded by the RNA molecule. Thus, the skilled worker presented with either the nucleotide sequence of an RNA molecule or the sequence of a gene encoding an RNA molecule is enabled to design an ASO which will efficaciously inhibit expression of the RNA molecule or gene by designing the ASO to be complementary to that portion of the RNA molecule which comprises a GGGA motif.

Definitions

As used herein, the term "flanking" is used to refer to nucleotide sequences which are directly attached to one another, having no intervening nucleotides. By way of example, the pentanucleotide 5'-AAAAA-3' is flanking the trinucleotide 5'-TTT-3' when the two are connected thus: 5'-AAAAATTT-3' or 5'-TTTAAAAA-3', but not when the two are connected thus: 5'-AAAAACTTT-3'. In the latter case, the C residue is said to be "interposed" between the pentanucleotide and the trinucleotide.

As used herein, the term "affected cell" refers to a cell in an animal afflicted with a disease or disorder, which affected cell has an altered phenotype relative to a cell of the same type in an animal not afflicted with the disease or disorder.

As used herein, the term "oligonucleotide" means a nucleic acid-containing polymer, such as a DNA polymer, an RNA polymer, or a polymer comprising both deoxyribonucleotide residues and ribonucleotide residues. This term further includes other polymers, such as polymers comprising modified or non-naturally-occurring nucleic acid residues and polymers comprising peptide nucleic acids. Each of these types of polymers, as well as numerous variants, are known in the art. This term includes, without limitation, both polymers which consist of nucleotide residues, polymers which consist of modified or non-naturally-occurring nucleic acid residues, and polymers which consist of peptide nucleic acid residues, as well as polymers comprising these residues associated with a support or with a targeting molecule, such as a cell surface receptor-binding protein.

As used herein, the term "antisense oligonucleotide" (ASO) means a nucleic acid polymer, at least a portion of which is complementary to a nucleic acid which is present in a normal cell or in an affected cell. The ASOs of the invention preferably comprise from twelve to about fifty nucleotide residues. More preferably, the ASOs comprise from fourteen to about thirty nucleotide residues. Most preferably, the ASOs comprise from sixteen to twenty-one nucleotide residues. The ASOs of the invention include, but are not limited to, phosphorothioate oligonucleotides and other modifications of oligonucleotides.

As used herein, the term "antisense agent" means an ASO suspended in a pharmaceutically acceptable carrier, whereby the ASO can be delivered to a cell of an animal, preferably a human. The term "antisense agent" includes naked DNA ASOs and naked RNA ASOs for delivery to a cell of an animal.

As used herein, the term "antisense therapy" means administration to an animal of an antisense agent for the purpose of alleviating a cause or a symptom of a disease or disorder with which the animal is afflicted.

As used herein, an oligonucleotide "associates" with another oligonucleotide or to a support to which the other oligonucleotide is linked when it binds to the other oligonucleotide in an affinity-dependent manner. By way of example, an oligonucleotide which hydrogen bonds to another oligonucleotide having a complementary nucleotide sequence when contacted therewith is said to associate with a support to which the other oligonucleotide is linked when the oligonucleotide is contacted with the medium.

As used herein, the term "binding energy" means the thermodynamic change in free energy which accompanies the binding of two complementary nucleic acids, one to the other. Binding energy is frequently expressed in terms of a change in the Gibbs free energy ($\Delta G$ or $\Delta G_{formation}$) at a given temperature.

"Complementary" refers to the broad concept of sequence complementarity between regions of two nucleic acid strands or between two regions of the same nucleic acid strand. A first region of a nucleic acid is complementary to a second region of the same or a different nucleic acid if, when the two regions are arranged in an antiparallel fashion, at least one nucleotide residue of the first region is capable of base pairing with a nucleotide residue of the second region. Preferably, when the first and second regions are arranged in an antiparallel fashion, at least about 50%, and preferably at least about 75%, at least about 90%, or at least about 95% of the nucleotide residues of the first region are capable of base pairing with nucleotide residues in the second region. Most preferably, all nucleotide residues of the first region are capable of base pairing with nucleotide residues in the second region (i.e. the first region is "completely complementary" to the second region). It is known that an adenine residue of a first nucleic acid strand is capable of forming specific hydrogen bonds ("base pairing") with a residue of a second nucleic acid strand which is antiparallel to the first strand if the residue is thymine or uracil. Similarly, it is known that a cytosine residue of a first nucleic acid strand is capable of base pairing with a residue of a second nucleic acid strand which is antiparallel to the first strand if the residue is guanine. It is understood that structure of nucleotide residues may be modified, whereby the complementation properties of the modified residue differs from the complementation properties of the naturally-occurring residue. Such modifications, and methods of effecting such modification, are known in the art.

As used herein, the term "complementary region of an RNA molecule" means a nucleotide sequence within an RNA molecule to which nucleotide sequence an ASO is complementary.

As used herein, an RNA molecule "corresponds" to a gene if the RNA molecule is generated upon transcription of the gene.

As used herein, an RNA molecule includes, without limitation, both the primary transcript ("pre-mRNA") obtained by transcribing a gene and a messenger RNA ("mRNA") obtained by transcribing a gene and processing the primary transcript.

As used herein, the term "gene" means a DNA sequence which, upon transcription thereof, yields an RNA molecule which encodes a protein and associated control sequences such as a translation initiation site, a translation stop site, a ribosome binding site, (optionally) introns, and the like. Alternately, the gene may be an RNA sequence which encodes a protein and associated control sequences such as a translation initiation site, a translation stop site, a ribosome binding site, and the like.

As used herein, the term "gene expression" includes both gene transcription, whereby DNA (or RNA in the case of some RNA-containing viruses) corresponding to a gene is transcribed to generate an RNA molecule and RNA translation, whereby an RNA molecule is translated to generate a protein encoded by the gene.

As used herein, the term "inhibition of gene expression" means inhibition of DNA transcription (or RNA transcription in the case of some RNA-containing viruses), inhibition of RNA translation, inhibition of RNA processing, or some combination of these.

As used herein, the term "oligonucleotide delivery agent" means a composition of matter which can be used to deliver an ASO to a cell in vitro or in vivo.

As used herein, the term "pharmaceutically-acceptable carrier" means a chemical composition with which an ASO of the invention may be combined and which, following the combination, can be used to administer the ASO of the invention to an animal.

As used herein, the term "protein expression" is used to refer both to gene expression comprising transcription of DNA (or RNA) to form an RNA molecule and subsequent processing and translation of the RNA molecule to form protein and to gene expression comprising translation of mRNA to form protein.

As used herein, the term "TNF-α-associated disease or disorder" means a disease or disorder of an animal which is caused by abnormal TNF-α expression or a disease or disorder which results in abnormal TNF-α expression, wherein abnormal TNF-α expression is determined relative to an animal not afflicted with the disease or disorder.

As used herein, the term "TNF-α-specific ASO" means an ASO which comprises a TCCC motif and which is complementary to an RNA molecule encoding TNF-α.

As used herein, the term "TCCC motif" means a tetranucleotide portion of an ASO, having the sequence 5'-TCCC-3'. It is understood that each of the four nucleotide residues of the TCCC motif may be any chemical entity which exhibits substantially the same complementarity properties as the residue it substitutes. Thus, the term TCCC motif includes any chemical entity which is capable of binding with a GGGA motif with substantially the same complementarity properties as a tetranucleotide portion of an ASO, having the sequence 5'-TCCC-3'.

As used herein, the term "GGGA motif" means a portion of an RNA molecule comprising a tetranucleotide having the sequence 5'-GGGA-3'.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The Efficacious ASO of the Invention

The invention relates to the surprising discovery that an ASO which comprises a TCCC motif and is complementary to an RNA molecule, such as an mRNA or, preferably, a primary transcript, corresponding to a gene is efficacious for inhibiting expression of the gene. The ASO of the invention is complementary to a region of an RNA molecule corresponding to a gene, wherein the region of the RNA molecule comprises at least one GGGA motif. Also preferably, the ASO comprises not more than one nucleotide which is not complementary to the RNA molecule corresponding to the gene.

The ASO of the invention comprises between about fourteen and about fifty nucleotides. Preferably, the ASO of the invention comprises between about twelve and about thirty nucleotides; even more preferably, it comprises between about sixteen and about twenty-one nucleotides. The invention also features an ASO which comprises at least a pair of flanking nucleotides having a phosphorothioate or other modified (i.e. non-phosphodiester) linkage. The gene may, for example, be a gene of a DNA or RNA virus. Preferably the gene is an animal gene; even more preferably it is a human gene.

Oligonucleotides which contain phosphorothioate modification(s) are known to confer upon the oligonucleotide enhanced resistance to nucleases. As many as all of the nucleotide residues of an ASO may be phosphorothioate-modified, as may as few as one residue. Specific examples of modified oligonucleotides include those which contain phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No. 5,034,506) or polyamide backbone structures (Nielsen et al., 1991, Science 254: 1497) may also be used. Oligonucleotides which are methylated or alkylated at the 2' hydroxyl position are also specifically included herein. These and other modified nucleotide residues, including peptide nucleic acids, for example, are known to those skilled in the art and are useful in the compositions and methods of the invention. Further by way of example, oligonucleotides comprising modified or non-naturally-occurring deoxyribonucleotide residues, modified or non-naturally-occurring ribonucleotide residues, or both, are likewise known and included in the compositions and methods of the invention.

The examples of oligonucleotide modifications described herein are not exhaustive and it is understood that the invention includes additional modifications of the ASOs of the invention which modifications serve to enhance the therapeutic properties of the ASO without appreciable alteration of the basic sequence of the ASO of the invention.

The antisense agents of the present invention may be incorporated in compositions suitable for a variety of modes of administration. One skilled in the art will appreciate that the optimal dose and methodology will vary depending upon the age, size, and condition of an animal. Optimal dose and route of administration are further dependent upon the bodily location of the organ, tissue, or cell to which the antisense agent of the invention is to be administered. Administration is generally continued until the cause or symptom of the disease or disorder is alleviated or cannot be detected.

Predicting the Efficacy of an ASO

The invention also includes a method for predicting whether an ASO will be efficacious for inhibiting expression of a gene, the method comprising determining whether the ASO is complementary to a portion of an RNA molecule corresponding to the gene, wherein that portion comprises a GGGA motif.

Methods of Making the Efficacious ASO of the Invention

The invention further includes a method for making an ASO which is efficacious for inhibiting expression of a gene having a corresponding RNA molecule. Such an ASO is made by synthesizing an oligonucleotide which comprises a TCCC motif and which is complementary to an RNA molecule corresponding to the gene. Methods for synthesizing an oligonucleotide having a selected nucleotide sequence are well known in the art. By way of example, a nucleotide sequence may be synthesized using an automated nucleotide synthesizing apparatus. The invention also includes, but is not limited to, ASOs made using this method.

The invention also includes an additional method of making an ASO which is efficacious for inhibiting expression of a gene having a corresponding RNA molecule which comprises an $S_1GGGAS_2$ sequence, wherein $S_1$ is a first RNA nucleotide sequence, and wherein $S_2$ is a second RNA nucleotide sequence. According to this method, the nucleotide sequence of the gene is obtained and a portion of the gene which encodes an $S_1GGGAS_2$ sequence in the corresponding RNA molecule is identified. The ASO is made by designing a nucleotide sequence which is complementary to the GGGA portion of the $S_1$ $GGGAS_2$ sequence and which is also complementary to at least a portion of one of the first RNA nucleotide sequence (i.e. $S_1$) and to at least a portion of the second RNA nucleotide sequence (i.e. $S_2$). The invention also includes ASOs made using this method.

Yet another method for making the ASO of the invention comprises making a plurality of ASOs, each of which comprises a TCCC motif and a randomly-generated sequence which flanks the TCCC motif on at least one side of the motif. Methods for synthesizing oligonucleotides comprising random sequences are well known in the art of molecular biology. The screening methods described herein may be used to screen the plurality of oligonucleotides to identify ASOs which are efficacious for inhibiting expression of a gene.

The ASOs of the invention include, but are not limited to, phosphorothioate oligonucleotides and other modifications of oligonucleotides. Methods for synthesizing oligonucleotides, phosphorothioate oligonucleotides, end-group-modified oligonucleotides, and otherwise modified oligonucleotides are known in the art (e.g. U.S. Pat. No. 5,034,506; Nielsen et al., 1991, Science 254: 1497).

Methods of Separating the Efficacious ASO from a Mixture of Oligonucleotides

The invention also includes methods of separating an ASO from a mixture of oligonucleotides, wherein the ASO is efficacious for inhibiting expression of a gene having a corresponding RNA molecule. These methods comprise contacting the mixture of oligonucleotides with a support which comprises a polynucleotide linked thereto, the polynucleotide comprising a portion having the sequence GGGA. After contacting the mixture with the support, the support is separated from the mixture, whereby efficacious ASOs remain bound to the support and are separated from the mixture. Various supports known in the art may be linked to the GGGA nucleotide sequence using known methods. By way of example, the sequence may be linked to cross-linked agarose beads or to a solid silica support. The polynucleotide may, for example, be all or a portion of the corresponding RNA molecule or a single strand of DNA having a nucleotide sequence homologous with the sequence of the corresponding RNA molecule.

Better separation of the efficacious ASO may be effected by treating the medium with an agent which causes dissociation of the efficacious ASO from the support. Once again, such agents are well known in the art and depend upon the type of support employed in the method. By way of example, when the support comprises the oligonucleotide comprising a portion which has a GGGA sequence linked to a solid silica matrix, the agent may be heat applied to a solution contacting the support, whereby the efficacious ASO dissociates from the support when the solution reaches the melting temperature of the ASO-oligonucleotide-GGGA sequence complex. Likewise by way of example, when the support is cross-linked agarose beads, agents such as solvents and salts, which interfere with hydrogen bonding between the ASO and the oligonucleotide comprising a portion which has a GGGA sequence, may be used to cause dissociation of the efficacious ASO from the support.

Another method for improving the separation of the efficacious ASO from the mixture comprises performing the methods described herein, and subsequently contacting the oligonucleotide mixture comprising the efficacious ASO with a second medium which comprises a portion of the corresponding RNA molecule linked to a second support.

Methods of Treating Diseases and Disorders Which are Characterized by the Presence of an RNA Molecule The invention features methods of treating diseases and disorders which are characterized by the presence in affected cells of an animal afflicted with the disease or disorder of an RNA molecule which corresponds to a gene. The RNA molecule may, for example, be one which is normally expressed in cells and expressed at an abnormal level in affected cells, or it may be one which is expressed only in affected cells, for example, one which is expressed only in affected cells by way of infection of the cell or abnormal gene expression in the cell. The molecule may be an mRNA molecule, for example, and is preferably a primary transcript. The methods comprise administering to the cells an antisense agent comprising an ASO of the invention which is efficacious for inhibiting expression of the gene.

The ASO may be administered to the animal to deliver a dose of between 1 ng/kg/day and 250 mg/kg/day. Preferably, the dose is between 5 mg/kg/day and 50 mg/kg/day. Antisense agents that are useful in the methods of the invention may be administered systemically in oral solid dosage forms, ophthalmic, suppository, aerosol, topical, intravenously-, intraperitoneally-, or subcutaneously-injectable, or other similar dosage forms. In addition to an ASO, such pharmaceutical compositions may contain pharmaceutically acceptable carriers and other ingredients known to enhance and facilitate drug administration. Other possible dosage forms, such as nanoparticles, liposomes, resealed erythrocytes, and immunologically based systems may also be used to administer the antisense agent according to the methods of the invention. Furthermore, antisense agents may be delivered using 'naked DNA' methods, wherein the oligonucleotides are not complexed with a carrier, or using viral vectors, such as adenoviral vectors or retroviral vectors.

Some examples of diseases and disorders which may be treated according to the methods of the invention are discussed herein. The invention should not be construed as being limited solely to these examples, as other diseases or disorders which are at present unknown, once known, may also be treatable using the methods of the invention.

Treatment of Inflammatory Diseases

The invention also features methods of treating inflammatory diseases which are associated with tumor necrosis factor alpha (TNF-α). TNF-α is a proinflammatory cytokine which exhibits pleiotropic effects on various cell types and tissues both in vivo and in vitro. Local expression of TNF-α is essential for cell homeostasis, but overexpression of TNF-α has been linked to numerous inflammatory conditions such as rheumatoid arthritis, systemic lupus erythmatosis, multiple sclerosis, leprosy, septic shock, and inflammatory bowel disease. Various studies have also established that TNF-α levels are greatly elevated in the plasma of humans afflicted with alcoholic hepatitis and cirrhosis, and that high TNF-α levels are correlated with mortality (McClain et al., 1986, Life Sci. 39:1474–1485; Felver et al., 1990 Alcohol. Clin. Exp. Res. 14:255–259; Bird et al., 1990, Ann. Int. Med. 112:917–920; Khoruts et al., 1991, Hepatol. 13:267–276; Sheron et al., 1991, Clin. Exp. Immunol. 84:449–453). Efforts to inhibit or control TNF-α overexpression are useful for the treatment of a number of conditions, including those discussed herein.

The invention includes a method of inhibiting expression of TNF-α. The method is useful for treating an animal afflicted with a TNF-α-associated disease or disorder. The method comprises administering a composition to an affected cell of an animal afflicted with a TNF-α-associated disease or disorder, which composition comprises an ASO which comprises a TCCC motif and which is complementary to an RNA molecule corresponding to a gene which encodes TNF-α. Preferably, the ASO is selected from the group of ASOs which consists of the ASOs having nucleotide sequences designated SEQ ID NOs: 19–27, SEQ ID NOs: 31–33, SEQ ID NOs: 44–55, SEQ ID NO: 57, SEQ ID NO: 58, SEQ ID NO: 60, and SEQ ID NO: 61. Given the homology that exists among animal TNF-α (and other) genes, a strategy similar to that described herein may be employed to design ASOs useful for inhibiting expression of TNF-α (and other) genes in a human.

The composition may also comprise an oligonucleotide delivery agent, such as a liposome, a plasmid, a nanoparticle projectile, a viral vector, or the like, for delivering the ASO to the interior of the affected cell. In view of the present disclosure, the skilled artisan is enabled to design ASOs specifically useful in humans using the nucleotide sequence of the human TNF-α gene.

For example, the nucleotide sequence of the human TNF-α gene has been described (Nedwin et al., 1985, Nucl. Acids Res. 13:6361; GenBank Accession Nos. X02910 and X02159; FIG. 4). By identifying GGGA motifs in the nucleotide sequence of the primary transcript of the human TNF-α gene, one skilled in the art may design ASOs which are effective for inhibiting expression of the human TNF-α gene by selecting a region of the primary transcript corresponding to the human TNF-α gene, the region having a length of from 12 to 50 nucleotide residues, preferably having a length between 14 and 30 nucleotide residues, and more preferably having a length between 16 and 21 nucleotide residues. The region also comprises a GGGA motif. The efficacious ASO is designed by designing a nucleotide sequence which is at least 90%, preferably at least 95% complementary, and most preferably 100% complementary to the nucleotide sequence of the selected region of the primary transcript. The efficacious ASO may comprise modified or non-naturally-occurring nucleotide residues, whereby the modified or non-naturally-occurring residues are capable of Watson-Crick-type base-pairing with the selected region of the primary transcript. Also preferably, the region of the primary transript is selected such that it comprises a GGGA motif which is flanked by regions having high purine content or which are otherwise able to assume an A-form conformation.

By way of example, ASOs which are efficacious for inhibiting expression of human TNF-α and which have a length of up to 21 nucleotide residues may be made by synthesizing oligonucleotides which are at least 90%, preferably at least 95%, and most preferably 100% complementary to one of the underlined or double-underlined regions in FIG. 4. Thus, an ASO which is efficacious for inhibiting expression of human TNF-α may have a nucleotide sequence which is complementary to up to, for example, sixteen to twenty-one consecutive nucleotide residues of the regions of the human TNF-α gene listed in Table 1, wherein the ASO is complementary to the GGGA motif in the region.

TABLE 1

| Region Designation | Nucleotide Residues[A] |
|---|---|
| I | 291–328 |
| II | 367–413 |
| III | 567–603 |
| IV | 645–682 |
| V | 801–838 |
| VI | 957–994 |
| VII | 1005–1169 |
| VIII | 1287–1324 |
| IX | 1333–1370 |
| X | 1414–1451 |
| XI | 1579–1616 |
| XII | 1695–1757 |
| XIII | 1900–1937 |
| XIV | 1967–2070 |
| XV | 2409–2446 |
| XVI | 2461–2498 |
| XVII | 2558–2595 |
| XVIII | 2865–2902 |
| XIX | 3090–3147 |
| XX | 3310–3347 |
| XXI | 3424–3461 |
| XXII | 3594–3634 |

Note:
[A]Nucleotide residues are identified using the numbering scheme used in Figure 4. The indicated regions are inclusive of the nucleotide residues identified as boundaries.

ASOs which are complementary to an mRNA molecule corresponding to a gene and which are efficacious may be designed by an analogous method, wherein the nucleotide sequence of the mRNA molecule is substituted in place of the nucleotide sequence of the primary transcript in the preceding paragraph.

Methods of Inhibiting Gene Expression

The invention further features methods of inhibiting the expression of a gene in a cell, which methods comprise administering to the cell an ASO of the invention.

When gene expression is to be inhibited in the cell in vitro, ordinary transfection techniques are used to effect entry of the oligonucleotide into the cell. When gene expression is to be inhibited in the cell in vivo, then the above-described procedures are followed.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLES

The materials and methods used in the experiments described in the Examples are now described.

Oligonucleotides

All phosphorothioate-modified oligonucleotides used in this study were synthesized and purified by Genset (La Jolla, Calif.). Prior to treatment of cells, oligonucleotides were sterilized by filtration through a filter having a pore diameter of 0.20 μm or through a filter having a pore diameter of 0.45 μm (Coming Glass Works, Coming, N.Y.) and stored at −70° C. Oligonucleotide concentrations in solution were determined spectrophotometrically by measuring the ratio of absorbance at 260 nanometers to absorbance at 280 nanometers.

Cell Lines

WEHI 164 and H4-IIIC cell lines were purchased from American Type Culture Collection (ATCC, Rockville, Md.).

Rat Kupffer cell isolation

Kupffer cells were isolated from male rats (300–400 g body weight) by sequential digestion of the rat livers using pronase and type 1 collagenase followed by elutriation, as described (Bautista et al., 1992, Gen. Leukoc. Biol. 51:39–45). Purity of Kupffer cell preparations was assessed by staining the cells for peroxidase activity and assessing the ability of the cells to phagocytose 1 micrometer latex beads (Kamimura et al., 1995, Hepatol. 21:1304–1309). Purity of Kupffer cell preparations exceeded 85% in every experiment described herein. Viability of cells in Kupffer cell preparations was assessed using the Trypan blue exclusion test, and always exceeded 95%.

Approximately $10^6$ Kupffer cells were transferred to individual 35 millimeter diameter dishes, and Kupffer cells were further purified using the adherence method, as described (Kamimura et al., 1995, Hepatol. 21:1304–1309). Cells were typically incubated in RPMI medium with 10% fetal bovine serum for one day following the adherence method procedure, prior to the use of the cells in in vitro experiments.

Treatment of Cells with ASO

ASOs were suspended in Lipofectamine A) (Life Technologies, Inc., Gaithersburg, MD), a cationic liposome, prior to delivery to cultured rat Kupffer cells, as described (Tu et al., 1995, J. Biol. Chem. 270:28402–28407). Up to 12 μg of an ASO and 8 μg of liposomes were diluted separately in 100 μl of Optimem M) (Life Technologies, Inc., Gaithersburg, Md.) reduced serum medium. The two suspensions were gently mixed and the combined suspension was incubated at room temperature for 45 minutes to form oligonucleotide-liposome complexes.

Kupffer cells were rinsed twice with Optimem® prior to the addition to the cell suspension of a mixture of 800 μl of Optimem® and 200 μl of the combined suspension, which comprised oligonucleotide-liposome complexes. Cells were exposed to the complexes for 4 hours at 37° C., 5% (v/v) $CO_2$, and 100% humidity. Antibiotics were not present in the cell culture medium during liposome-mediated delivery.

Following treatment with the oligonucleotide-liposome complexes, the medium was removed, and the cells were washed twice with 37° C. Optimem® and cultured in RPMI medium with 10% fetal bovine serum for an additional 17 hours. Tumor necrosis factor-α (TNF-α) expression was induced by addition to the cell culture medium of 10 ng/ml of lipopolysaccharide (LPS) for 2 hours. Following LPS treatment, the culture medium was removed and cells were stored at -70° C. until TNF-α assays were performed. Cells were rinsed twice with cold phosphate-buffered saline (PBS) and were lysed using a 5% (w/v) SDS solution prior to protein determination.

Extraction of Cellular RNA and Protein

Total cellular RNA was prepared from PBS-rinsed cells using Tri Reagent® (Life Technologies, Inc., Gaithersburg, Md.) as described (Tu et al., 1995, J. Biol. Chem. 270:28402–28407). RNA concentration was determined by measuring the ratio of absorbance at 260 nanometers to absorbance at 280 nanometers using a Beckman DU-640 spectrophotometer.

Total cellular protein was prepared by lysing PBS-rinsed cells using a 5% (w/v) SDS solution at room temperature overnight. Protein concentrations were determined using a MicroBCA protein assay kit (Pierce, Rockford, Ill.) according to the manufacturer's instruction.

TNF-α Assays

TNF-α in cell culture supernatants was assayed by bioassay and ELISA methods. The bioassay was performed as described (Kamimura et al., 1995, Hepatol. 21:1304–1309), using WEHI 164 cells as a assay reactant. ELISA was conducted by using a Cytoscreen KRC3012 ELISA kit (Biosource, Camarillo, Calif.) according to the manufacturer's specifications. Supernatants containing a high level of TNF-α were diluted prior to assay to ensure reliable assay results. All samples were assayed in triplicate.

Northern Hybridization

Total cellular RNA was isolated as described (Tu et al., 1995, J. Biol. Chem. 270:28402–28407). A Northern blot was prepared using 5 micrograms of total RNA per lane, and was probed using $^{32}$P-labeled cDNA encoding murine TNF-α, as described (Kamimura et al., 1995, Hepatology 22:1304–1309). Densitometric analysis of TNF-α mRNA was standardized by comparison with 18S rRNA hybridization.

Other methods which were used but not described herein are well known and within the competence of one of ordinary skill in the art of antisense technology and molecular biology.

Example 1

Screening ASOs Which are Efficacious for Inhibiting TNF-α Expression

Based upon the primary transcript sequence of rat TNF-α (Shirai et al., 1989, Agric. Biol. Chem. 53:1733–1736), seventeen phosphorothioate-modified ASOs were designed which were complementary to different regions of the primary transcript, including the 5'-cap site, the translation initiation codon, various exon/intron junctions, the stop codon, and the 3'-untranslated region, as indicated in Table 2. The ability of each of these ASOs to inhibit expression of rat TNF-α in cultured rat Kupffer cells which were stimulated using bacterial lipopolysaccharide (LPS) was assessed by contacting aliquots of the cells with individual ASOs, culturing the aliquots for about seventeen hours, and then assessing TNF-α expression in the cells.

ASOs were delivered into cultured rat Kupffer cells using cationic liposomes (Lipofectamineg, Life Technologies, Inc., Gaithersburg, MD). Cationic liposomes have been demonstrated to enhance cellular uptake and biological activity of phosphorothioate-modified oligonucleotides (Bennett et al., 1992, Mol. Pharmacol. 41:1023–1033; Bennett et al., 1993, J. Liposome Res. 3:85–102; Tu et al., 1995, J. Biol. Chem. 270:28402–28407). Although high concentrations of liposome has been reported to be toxic to some cell lines (Bennett et al., 1992, Mol. Pharmacol. 41:1023–1033), treatment of cultured rat Kupffer cells with 8 μg/ml Lipofectamine(V for 4 hours did not inhibit rat TNF-α expression in Kupffer cells following LPS stimulation.

Table 2 summarizes results obtained using ASOs to inhibit rat TNF-α as described herein. Oligonucleotides having the sequence indicated in the table were synthesized and used to treat cultured rat Kupffer cells, as described herein. Expression of TNF-α protein was assessed following incubation of the cells and stimulation using LPS. TNF-α expression is reported in Table 2 as a mean percentage (±standard deviation) of TNF-α expression in control cells which were not treated with an ASO. Each ASO in Table 2 is reported using an identifier, a SEQ ID NO, a sequence listing, and an indication of the region of the primary transcript encoding rat TNF-α to which the ASO was designed to be complementary. "Putative tsp" denotes an ASO comprising a sequence complementary to the putative transcription start point. "AUG codon" denotes an ASO comprising a sequence complementary to the translational initiation site. "Ex. #/In. ##" denotes an ASO comprising a sequence complementary to the junction between exon # and intron ## of the RNA molecule encoding rat TNF-α. "3'-Untr. Reg." denotes an ASO comprising a sequence complementary to a portion of the 3'-untranslated region of the RNA molecule encoding rat TNF-α. "Activation" denotes TNF-α expression which exceeded TNF-α expression which was observed in control cells.

TABLE 2

| Identifier | SEQ. ID NO: | Oligonucleotide sequence (5'→3') | Region of primary transcript | TNF-α Prod. (% Con) |
|---|---|---|---|---|
| TJU-0641 | 1 | CCTCGCTGAGTTCTGCCGGCT | putative tsp | 97 ± 8.9 |
| TJU-0796 | 2 | CCGTGCTCATGGTGTCCTTTC | AUG codon | 52 ± 5.7 |
| TJU-0807 | 3 | GATCATGCTTTCCGTGCTCAT | AUG codon | 93 ± 7.8 |
| TJU-0981 | 4 | GGCACTCACCTCCTCCTTGTT | Ex. 1/In.1 | 94 ± 7.2 |
| TJU-1534 | 5 | ACACTTACTGAGTGTGAGGGT | Ex. 2/In.2 | 110 ± 8.5 |
| TJU-1730 | 6 | AAACTTACCTACGACGTGGGC | Ex. 3/In.3 | 110 ± 9.7 |
| TJU-2431 | 7 | GTCGCCTCACAGAGCAATGAC | Ex. 4/STOP | activation |
| TJU-2507 | 38 | TAGACGATAAAGGGGTCAGAG | 3'-Untr. Reg. | ca. 115 |
| TJU-2698 | 8 | AGTGAGTTCCGAAAGCCCATT | 3'-Untr. Reg. | 93 ± 8.2 |
| TJU-2719 | 9 | GGCATCGACATTCGGGGATCC | 3'-Untr. Reg. | 85 ± 6.4 |
| TJU-2755 | 10 | TGATCCAC<u>T</u>CCCCCCTCCACT | 3'-Untr. Reg. | 7.7 ± 5.1 |
| TJU-2779 | 11 | CAGCCTTGTGAGCCAGAGGCA | 3'-Untr. Reg. | 110 ± 9.4 |
| TJU-2800 | 12 | GGAGGCCTGAGACATCTTCAG | 3'-Untr. Reg. | 100 ± 8.8 |
| TJU-2819 | 13 | AGGGAAGGAAGGAAGGAAGGG | 3'-Untr. Reg. | activation |
| TJU-2826 | 14 | CTGAGGGAGGGAAGGAAGGAA | 3'-Untr. Reg. | 120 ± 9.8 |
| TJU-2840 | 39 | CAGTCTGGGAAGCTCTGAGGG | 3'-Untr. Reg. | ca. 115 |
| TJU-2879 | 15 | GGTTCCGTAAGGAAGGCTGG | 3'-Untr. Reg. | 93 ± 7.2 |
| TJU-2927 | 16 | AATAATAAATAATAAATAAAT | 3'-Untr. Reg. | 99 ± 8.3 |
| TJU-2991 | 17 | TTCCCAACGCTGGGTCCTCCA | 3'-Untr. Reg. | 98 ± 9.9 |
| TJU-3050 | 40 | GGGATAGCTGGTAGTTTAG | 3'-Untr. Reg. | ca. 100 |
| TJU-3260 | 41 | CATTTCTTTTCCAAGCGAAC | 3'-Untr. Reg. | ca. 90 |
| TJU-3428 | 42 | AGGCTCCTGTTTCCGGGGAGA | 3'-Untr. Reg. | ca. 120 |
| TJU-2734 | 18 | CCCCCGATCCACTCAGGCATC | 3'-Untr. Reg. | 82 ± 6.7 |
| TJU-2737 | 19 | AC<u>TCCCC</u>CGATCCACTCAGGC | 3'-Untr. Reg. | 14 ± 5.3 |
| TJU-2740 | 20 | TCCAC<u>TCCCC</u>CGATCCACTCA | 3'-Untr. Reg. | 7.9 ± 4.3 |
| TJU-2743 | 21 | CCCTCCAC<u>TCCCC</u>CGATCCAC | 3'-Untr. Reg. | 7.5 ± 4.6 |
| TJU-2746 | 22 | CCCCCCTCCAC<u>TCCCC</u>CCGATC | 3'-Untr. Reg. | 8.2 ± 4.7 |
| TJU-2749 | 23 | AC<u>TCCCC</u>CCTCCAC<u>TCCCC</u>CG | 3'-Untr. Reg. | 9.1 ± 5.4 |
| TJU-2752 | 24 | TCCAC<u>TCCCC</u>CCTCCACTCCC | 3'-Untr. Reg. | 7.9 ± 4.4 |
| TJU-2755 | 25 | TGATCCAC<u>TCCCC</u>CCTCCACT | 3'-Untr. Reg. | 7.7 ± 5.1 |
| TJU-2758 | 26 | GCCTGATCCAC<u>TCCCC</u>CCTCC | 3'-Untr. Reg. | 8.2 ± 4.2 |

TABLE 2-continued

| Identifier | SEQ. ID NO: | Oligonucleotide sequence (5'→3') | Region of primary transcript | TNF-α Prod. (% Con) |
|---|---|---|---|---|
| TJU-2761 | 27 | GCAGCCTGATCCACTCCCCCC | 3'-Untr. Reg. | 15 ± 6.2 |
| TJU-2764 | 28 | GAGGCAGCCTGATCCACTCCC | 3'-Untr. Reg. | 98 ± 11 |
| TJU-2755SS | 29 | AGTGGAGGGGGAGTGGATCA | | activation |
| TJU-2755RD | 30 | CCCTCACTGCTACCTCACCTC | | 89 ± 7.0 |
| TJU-2749-19 | 31 | ACTCCCCCCTCCACTCCCC | 3'-Untr. Reg. | 8.6 ± 4.1 |
| TJU-2740-18 | 32 | TCCACTCCCCCGATCCAC | 3'-Untr. Reg. | 7.8 ± 4.0 |
| TJU-2755-16 | 33 | TGATCCACTCCCCCCT | 3'-Untr. Reg. | 8.4 ± 4.3 |

The first twenty-two ASOs listed in Table 2, most of which were selected randomly, and some (i.e. SEQ ID NOs: 38–42) of which were predicted to be efficacious using the methods described herein, were each examined for the ability to inhibit TNF-α expression in cultured cells when the ASO was present in the cell culture medium at a concentration of 1 micromolar. Only one of the ASOs, TJU-2755, inhibited the expression of TNF-α by at least 90% compared with control cells. TJU-2755 comprised a sequence complementary to a portion of the 3'-untranslated region of the RNA molecule. Another oligonucleotide, TJU-0796, inhibited TNF-α expression but with an efficacy of only 50%. The remaining oligonucleotides either had no effect on TNF-α expression or actually activated TNF-α expression. As indicated in FIG. 1, inhibition of TNF-α expression by TJU-2755 is dose-dependent, and the value of $I_{50}$, the concentration of TJU-2755 in the culture medium which was necessary to effect 50% inhibition of TNF-α expression, was approximately 0.1 micromolar.

To test the specificity of TJU-2755 inhibition of TNF-α expression, two control oligonucleotides were examined at a concentration of 2 micromolar in the culture medium. A scrambled oligonucleotide, TJU-2755-RD, having the same nucleotide composition as TJU-2755 but in random order, and a sense oligonucleotide TJU-2755-SS, which was complementary to TJU-2755, were assessed for the ability to inhibit TNF-α expression. Neither TJU-2755-RD nor TJU-2755-SS inhibited TNF-α expression in cultured rat Kupffer cells. This result indicated that the inhibitory effect of TJU-2755 on TNF-α expression was markedly dependent on the nucleotide sequence of TJU-2755.

Ten additional oligonucleotides were designed and synthesized, each of which comprised a TCCC motif. The ability of each of these ASOs (SEQ ID NO: 18 through SEQ ID NO: 26 and SEQ ID NO: 28 in Table 2) to inhibit TNF-α expression was assessed as described herein. It was determined that all ASOs which inhibited TNF-α expression by at least about 80% comprised at least one full TCCC motif (Table 2). The data also establish that ASOs comprising a TCCC motif can comprise fewer than twenty-one, and as few as sixteen or fewer, nucleotide residues (e.g. TJU-2749-19, TJU-2740-18 and TJU-2755-16 in Table 2).

Each of the ASOs indicated in Table 2 which inhibited TNF-α expression comprised a TCCC motif and was complementary to an RNA molecule encoding rat TNF-α. This demonstrates that a TNF-ct-specific ASO can be designed by designing an ASO including a TCCC motif and flanking TNF-α nucleotide sequence(s). Although only TNF-α-specific ASOs comprising between sixteen and twenty-one nucleotide residues have been described herein, it is clear, given the data presented herein, that TNF-α-specific ASOs may be designed which comprise more than twenty-one or fewer than sixteen nucleotide residues by including a TCCC motif and at least one flanking TNF-α nucleotide sequence in the ASO. Preferably, such ASOs comprise no more than one nucleotide residue which is not complementary to a TNF-α-encoding RNA molecule. The ability of these oligonucleotides to inhibit TNF-α expression may be easily assessed using the screening methods described herein.

A number of mechanisms are known by which ASOs are capable of inhibiting protein expression, including translational arrest, inhibition of RNA processing, and promotion of RNase H-mediated degradation of the RNA component of the RNA-oligonucleotide complex (Crook, 1993, FEBS J. 7:533–539). A DNA-RNA heteroduplex of 4 to 6 nucleotides in length is sufficient to evoke RNase H activity (Kramer et al., 1984, Cell 38:299–307). Bennett et al. (1991, J. Immunol. 152:3530–3540) demonstrated that ASOs inhibited human ICAM-1 and E-selectin gene expression by two distinct mechanisms. Oligonucleotides which were complementary to the 3'-untranslated region of either gene (ISIS 1939, ISIS 2302, and ISIS 4730) reduced the corresponding mRNA levels, which suggested that RNase H-mediated degradation mechanism was responsible for the inhibition of gene expression. Oligonucleotides which were complementary to region around the AUG translation initiation codon (ISIS 1750 and ISIS 2679) did not alter mRNA levels, which suggested that translational arrest was responsible for the inhibition of gene expression.

Example 2

The Presence of the TCCC Motif in Reported Efficacious ASOs

A comprehensive search was conducted using the MEDLINE database, current through September 1997, to identify efficacious ASOs which had been reported in the literature. These sequences were examined to determine whether a higher proportion of the sequences comprised a TCCC motif than would be expected by random occurrence of these motifs.

For this literature search, the following conditions were imposed. Only ASOs selected from among 10 or more ASOs as being effective were included. Only ASOs selected from among ASOs designed to target a broad range of RNA regions were included in the search. ASOs presently in FDA-approved human clinical trials were also included in the search.

A total of 42 ASOs complied with these conditions. A TCCC motif was identified in 20 of these ASOs (48%). The nucleotide sequences of the most effective known ASOs comprising the TCCC motif are listed in Table 3. Chi-square analysis indicates that the probability of one TCCC motif existing by chance in 20 of 42 ASOs is remote ($p \ll 0.001$; $\chi^2 = 34.8$). By comparison, a VCCC motif (i.e. V is A, G, or C, but not T), the sequence was only found in 5 of the 42 most effective ASO sequences. In only two effective known ASOs was the TCCC motif located at the end of the ASO. Thus, it appears that the TCCC motif should be flanked on both sides by non-TCCC motif nucleotide residues that are complementary to nucleotide sequences which flank the GGGA motif of the corresponding RNA molecule.

In Table 3, 20 of the 42 most efficacious ASOs which have been reported in the literature are listed. Each of these ASOs comprises a TCCC motif. The ASOs are grouped according to the nucleotide residue at the 3'-end of the TCCC motif. For each of the ASOs listed, the identifier used in the reported study is indicated, and the reference number corresponding to the study is listed in parentheses beneath the identifier. A list of citations follows the table. The TCCC motif is underlined in each sequence listing. "mRNA" refers to the region of the corresponding mRNA molecule to which the indicated ASO reported in the study was complementary, and indicates the species and protein corresponding to the mRNA molecule. Where known, the region of the mRNA molecule to which the indicated ASO was complementary is indicated parenthetically. "3'-UTR" refers to the 3'-untranslated region of the mRNA molecule. "AUG" refers to a region comprising the AUG translation initiation codon of the mRNA molecule. "Stop codon" refers to a region comprising a translation stop codon of the mRNA molecule. "5'-UTR" refers to the 5'-untranslated region of the mRNA molecule. "Efficacy" refers to the approximate degree to which gene expression was inhibited in the study. Where only data corresponding to mRNA levels are reported in the indicated study, "M.E." refers to the oligonucleotide of the study which had the maximum effect. "# tested" refers to the number of oligonucleotides which were compared in the indicated study. "ICAM" means intercellular adhesion molecule. "VCAM" means vascular cell adhesion molecule. "PKC" means protein kinase C. "PAI" means plasminogen activator inhibitor. "NGF" means nerve growth factor. "Xklp" means Xenopus kinesin-like protein. HCV means the 5'-untranslated region of HCV.

TABLE 3

| Identifier (Ref. #) | mRNA | Inhibitory Oligonucleotide Sequence (listed 5'-3') | # tested |
|---|---|---|---|
| A. ASOs comprising a TCCC motif, followed by C | | | |
| OL(1)p53[1] | Human p53(ORF) | CCTGCTCCCCCCTGGCTCC | hum. trials |
| ISIS 1939[2,3] | Human ICAM-1(3'-UTR) | CCCCCACCACTTCCCCTCTC | 45 |
| GM 1508[4] | Human ICAM-1(3'-UTR) | CCCCCACCACTTCCCCTCTCA | 39 |
| ISIS 4189[5] | Murine PKC-α(AUG) | CAGCCATGGTTCCCCCCAAC | 20 |
| ISIS 4730[2] | Human E-selectin(3'-UTR) | TTCCCCAGATGCACCTGTTT | 18 |
| ISIS 11300[6] | Rat PKC-α(ORF) | GACATCCCTTTCCCCCTCGG | 13 |
| C15[7] | 1.19CAT(5'-UTR) | GATCCCCGGGTACCGA | 13 |
| ISIS 3890[8] | Human PKC-α(AUG) | GTCAGCCATGGTCCCCCCCC | 20 |
| Oligo 7[9] | Xenopus Xklp-1 | ATGCCCTCATCCTTCCCCCAT | >9 |
| B. ASOs comprising a TCCC motif, followed by A | | | |
| G 3139[10] | Human bcl-2 (ORF | GTTCTCCCAGCGTGTGCCAT | hum. trials |
| GM 1534[4] | Human VCAM-1(5'-UTR) | AACCCTTATTTGTGTCCCACC | 28 |
| ODN 2309[11] | Murine tPA (5'-UTR) | GTCCCAAGAGTTGAGGAG | 18 |
| ISIS 3466[12] | Human p120 (3'-UTR) | CACCCGCCTTGGCCTCCCAC | 18 |
| C. ASOs comprising a TCCC motif, followed by G | | | |
| ISIS 5132[13] | Human C-raf | TCCCGCCTGTGACATGCATT | hum. trials |
| ISIS 5995[14] | Human MDR-1 (AUG) | CCATCCCGACCTCGCGCT | 32 |
| T 195[15] | Human TNF (ORF) | CCACGTCCCGGATCATGC | 15 |
| D. ASOs comprising a TCCC motif, followed by T | | | |
| 4484-4503[16] | Human HIV (SA) | TCTGCTGTCCCTGTAATAAA | 20 |
| ISIS 3801[3] | Human VCAM | AACCCAGTGCTCCCTTTGCT | 15 |
| E. ASO comprising a TCCC motif at the 3'-end thereof | | | |
| ISIS 3522[17] | HumanPKC-α(AUG) | AAAACGTCAGCCATGGTCCC | 20 |

The references indicated in Table 3 are:

[1] Bishop et al., 1996, J. Clin. Oncol. 14:1320–1326
[2] Chiang et al., 1991, J. Biol. Chem. 266:18162–18171
[3] Bennett et al., 1994, J. Immunol. 152:3530–3540
[4] Lee et al., 1995, Shock 4:1–10
[5] Dean et al., 1994, Proc. Natl. Acad. Sci. U.S.A. 91:11762–11766
[6] Dean et al., 1996, Biochem. Soc. Trans. 24:623–629
[7] johansson et al., 1994, Nucl. Acids Res. 22:4591–4598
[8] Dean et al., 1994, J. Biol. Chem. 269:16146–16424
[9] Vemos et al., 1995 Cell 81:117–127
[10] Cotter et al., 1994, Oncogene 9:3049–3055
[11] Stutz et al., 1997, Mol. Cell. Biol. 17:1759–1767
[12] Perlaky et al.,1993, Anti-cancer Drug Des. 8:3–14
[13] Monia et al., 1996, Nature Med. 2:668–675
[14] Alahari et al., 1996, Mol. Pharmacol. 50:808–819
[15] d'Hellencourt et al., 1996, Biochim. Biophys. Acta 1317:168–174
[16] Goodchild et al., 1988, Proc. Natl. Acad. Sci. USA 85:5507–5511
[17] Dean et al., 1994, J. Biol. Chem. 269:16416–16424

Hence, it is clear that 5'-TCCC-3' is a nucleotide motif which confers surprising efficacy on ASOs which comprise the sequence. Because it is well known in the art that uridine has nucleotide binding properties analogous to those of thymidine, one of skill in the art will recognize that T may also be U.

Therefore, it has been demonstrated herein that ASOs which are efficacious for inhibiting expression of genes comprising a corresponding RNA molecule may be made by selecting an ASO comprising a nucleotide sequence which comprises a TCCC motif. That is, ASOs which are efficacious for inhibiting expression of genes comprising a corresponding RNA molecule may be made by selecting an ASO comprising a nucleotide sequence complementary to a region of the corresponding RNA molecule, wherein the region comprises a GGGA motif.

Preferably, the TCCC motif is flanked on both sides by nucleotide sequences which are complementary to the corresponding RNA molecule.

It is significant that the efficacy of ASOs which comprise a TCCC motif has been demonstrated in numerous animal species, including rat (described herein), human, mouse, chicken, and toad (each described in studies summarized in Table 3).

The skilled artisan will recognize that because no significant difference exists among animals, and particularly between vertebrates, in the ability of an ASO to undergo hybridization in a cell of an animal, the methods and compositions described herein are equally applicable in all animal species.

Example 3

Prospective Design of ASOs Which are Efficacious for Inhibiting TNF-α Expression In this Example, a series of ASOs were designed to target each of the GGGA motifs identified in an RNA molecule encoding rat TNF-α. Based on the published sequence of the rat TNF-α gene (Shirai et al., 1989, Agric. Biol. Chem. 53:1733–1736), twenty-eight GGGA motifs exist in the region of the primary transcript of this gene which is located on the 5'-side of the AATAAA polyadenylation site and another three GGGA motifs exist in the region of the primary transcript which is located on the 3'-side of that site. These motifs are located in introns 1–3, in exon 4, and in both the 5'- and 3'-untranslated regions. None of the motifs are located in exon 1, exon 2, or exon 3 of the rat TNF-α gene.

The nucleotides sequences of the twenty-five ASOs which were used in this Example are listed in Table 4, which also lists the sequences of ASOs designated TJU-2740 and TJU-2755, which are described elsewhere herein. Among these ASOs, six were designed to be complementary to TNF-α-encoding RNA regions comprising either two flanking GGGA motifs or two GGGA motifs comprising no more than six nucleotide residues interposed therebetween. The other ASOs were designed to be complementary to TNF-α-encoding RNA regions comprising only one GGGA.

Table 4

| Name of ASO | Nucleotide Sequence (5'-3') | SEQ ID NO: | $T_m$, °C. |
|---|---|---|---|
| TJU-0656 | CTGG<u>TCCC</u>TTGGTGTCCTCGC | 43 | 60.2 |
| TJU-0675 | TTGCTGTTC<u>TCCC</u>TCCTGGCT | 44 | 56.3 |
| TJU-1032 | TTCTTGCCC<u>TCCC</u>TCCCTACT | 45 | 56.3 |
| TJU-1056 | CCTCTTT<u>TCCC</u>TTACCCTCCTG | 46 | 56.3 |
| TJU-1103 | GGTC<u>TCCC</u>TCCCCAACTCTCC | 47 | 60.2 |
| TJU-1227 | CTTCTT<u>TCCC</u>TGTT<u>CCCC</u>TGGC | 48 | 58.3 |
| TJU-1271 | TATC<u>TCCC</u>TCGTC<u>TCCC</u>ATCT | 49 | 54*4 |
| TJU-1310 | GTTT<u>CCCC</u>TCCATC<u>TCCC</u>TCC | 50 | 58.3 |
| TJU-1424 | GAAGCC<u>TCCC</u>CGCTCTTTGCC | 51 | 60.2 |
| TJU-1585 | AAAGCTTTAAG<u>TCCC</u>CCGCCC | 52 | 56.3 |
| TJU-1608 | CCTATT<u>CCC</u>TTTCC<u>TCCC</u>AAA | 53 | 52.4 |
| TJU-1646 | CCCTTAGGTTT<u>CCC</u>AGCAAGC | 54 | 56.3 |
| TJU-1906 | CTGGTCTTTCCACG<u>TCCC</u>ATT | 55 | 54.4 |
| TJU-2161 | GCAGCCTTG<u>TCCC</u>TTGAAGAG | 56 | 56.3 |
| TJU-2287 | CTTGAGCTCAGC<u>TCCC</u>TCAGG | 57 | 58.3 |
| TJU-2327 | GCTGGAAGACTCC<u>TCCC</u>AGGT | 58 | 58.3 |
| TJU-2350 | GCTGAGCAGG<u>TCCC</u>CCTTCTC | 59 | 60.2 |
| TJU-2561 | AGAGCCACAATT<u>CCC</u>TTTCTA | 60 | 50.5 |
| TJU-2740 | TCCAC<u>TCCC</u>CCGATCCACTCA | 20 | 58.3 |
| TJU-2755 | TGATCCAC<u>TCCC</u>CCCTCCACT | 10 | 58.3 |
| TJU-3004 | GCCTGAAGACAGCT<u>TCCC</u>AAC | 61 | 56.3 |
| TJU-3208 | CAGTCACGGC<u>TCCC</u>GTGGG | 62 | 59.7 |
| TJU-3466 | GGGAAATT<u>CCC</u>AGGACCAGGG | 63 | 58.3 |
| TJU-3484 | ATTTGGAAT<u>TCCC</u>AGAGTGGG | 64 | 52.4 |
| TJU-3499 | ACTT<u>TCCC</u>AGCAGGTATTTGG | 65 | 52.4 |

Figure 2:
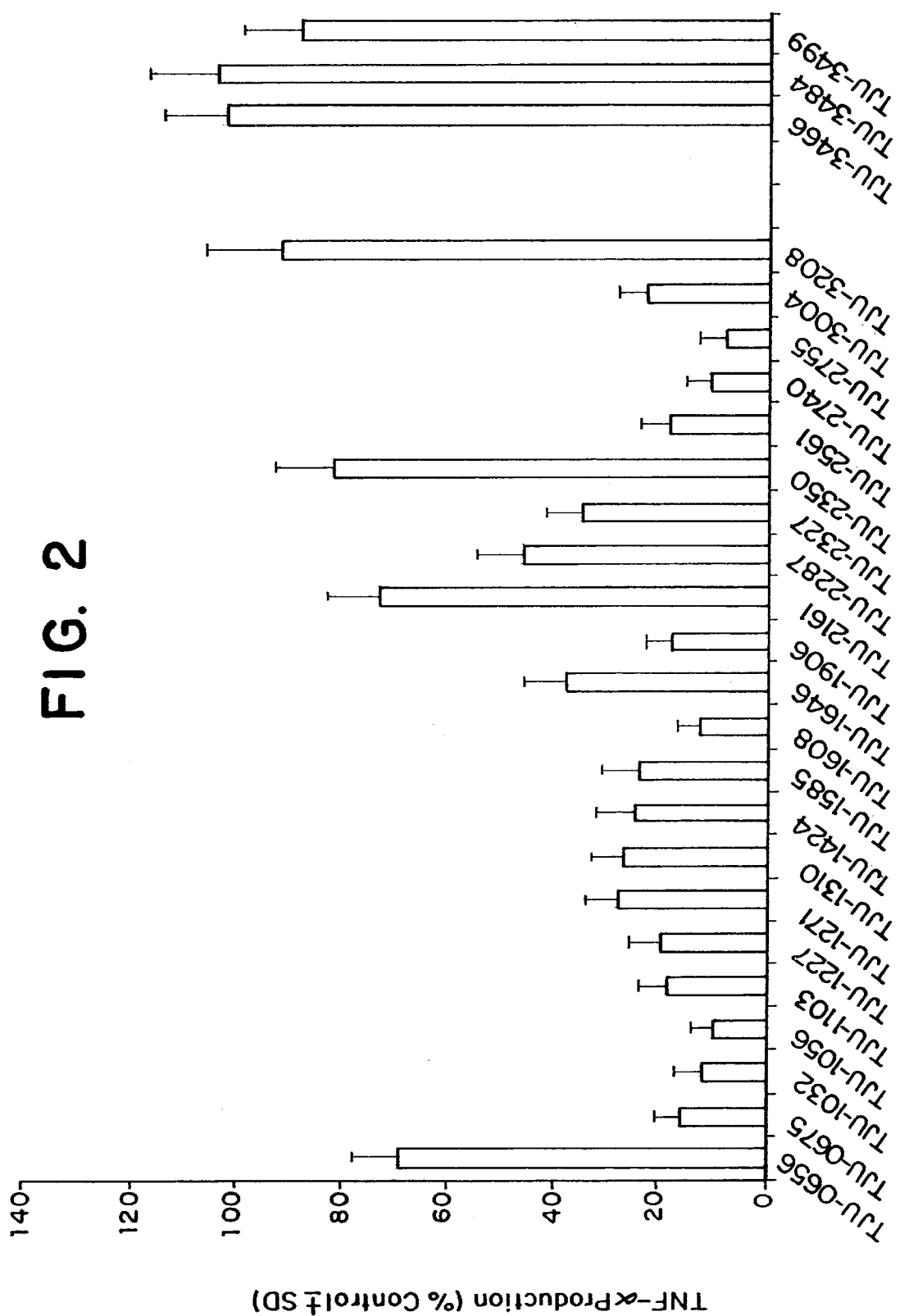
FIG. 2 is a bar graph which indicates the inhibition of TNF-α expression achieved by culturing cells in the presence of the indicated ASOs.

The ability of the ASOs described in this Example to inhibit TNF-α expression was assessed as described herein using an ASO concentration of 1 micromolar. As indicated in FIG. 2, more than half (13/22) of the ASOs described in this Example inhibited TNF-α expression by 75% or more. Seven of the ASOs described in this Example did not significantly inhibit TNF-α expression, including all three of the ASOs designed to be complementary to a GGGA motif located on the 3'-side of the AATAAA polyadenylation site of TNF-α-encoding RNA.

Figure 3:
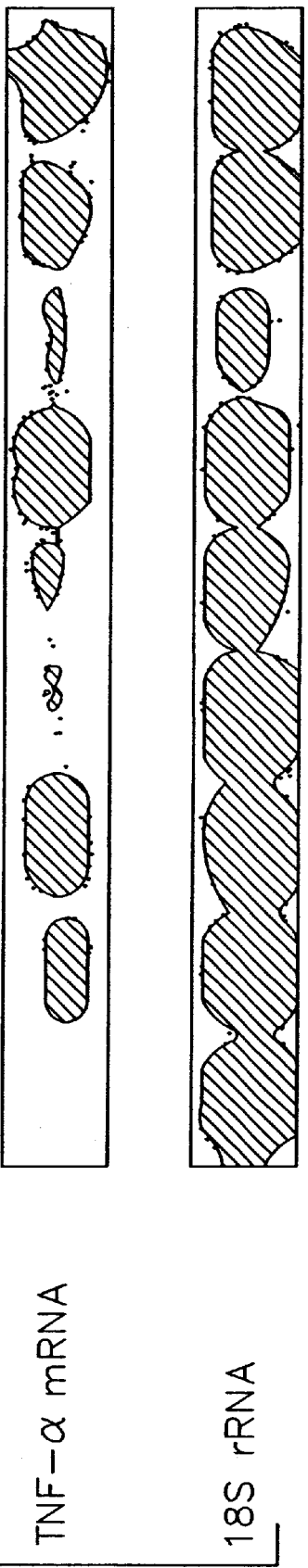
FIG. 3 is an image which portrays the results of Northern hybridization experiments described herein in Example 4. "Motif containing" refers to whether the ASO used in the corresponding lane comprised a TCCC motif.

The effect of the presence of several of the ASOs described in this Example on the steady-state level of mRNA encoding TNF-α was assessed by Northern analysis of RNA obtained from cells cultured in the presence of these ASOs. The results of these Northern analyses are summarized in FIG. 3. It is evident in FIG. 3 that levels of mRNA encoding TNF-α were depressed in cells which were cultured in the presence of ASOs which inhibited expression of TNF-α (i.e. lanes 4, 5, and 7, corresponding to cells cultured in the presence of TJU-2755, TJU-1906, and TJU-3004, respectively). Levels of 18S RNA were unaffected.

Without wishing to be bound by any particular theory, it is hypothesized that these results indicate that inhibition of TNF-α expression by these ASOs occurs by a mechanism which promotes degradation of RNA molecules encoding TNF-α. The fact that TNF-α-inhibitory ASOs were complementary to regions of the primary transcript comprising a GGGA motif suggests that the expression-inhibiting effect is exerted in the nucleus, before the primary transcript is spliced. This hypothesis is consistent with reports that ASOs rapidly accumulate in the nucleus after being introduced directly into the cell cytoplasm by microinjection, electroporation, streptolysin O treatment, or cationic liposome delivery (Giles et al., 1995, Antisense Res. Dev. 5:23–31).

Therefore, while remaining not bound by any particular theory of operation, it is hypothesized that ASOs, RNases and newly synthesized RNA molecules are present in the nucleus following delivery of an ASO to a cell. The nucleus is the primary site at which ASOs exert their gene-expression-inhibiting effect. The primary transcript of the expression-inhibited gene is the physiological target with which the ASO interacts, rather than the mature mRNA corresponding to that gene. It may be that the mechanism by which an ASO effects primary transcript degradation involves a nuclear RNase.

According to this hypothesis, RNA regions comprising an GGGA motif may be preferred sites for RNase digestion. This hypothesis is supported by the observations of Lima and Crooke (1997, Biochemistry 36:390–398), which indicated that although RNase H was not highly specificity with regard to the nucleotide sequence of the DNA-RNA hybrid on which it acts, it preferentially bound to the A-form of a DNA-RNA duplex. Since RNA sequences containing high purine content are predicted to stack in the A-form conformation (Ratmeyer et al., 1994, Biochemistry 33:5298–5304), RNase H activity may be improved using ASOs containing pyrimidine-rich sequences (i.e. which are complementary to RNA molecules which have purine-rich sequences and which therefore are likely to assume the A-form conformation). As can be ascertained by reviewing the nucleotide sequences listed in Table 4, both the TCCC motif itself and the bases at either end of the motif are pyrimidine-rich in the most potent ASOs.

This hypothesis may help explain why many ASOs designed by others were not efficacious. Most of ASOs reported in the literature were designed to target a region of a mature mRNA molecule, rather than a region of the corresponding primary transcript. For example, about 70% of reported ASOs were designed to target the mRNA region comprising the AUG codon. Were these ASOs instead designed to be complementary to a region of the primary transcript, particularly a region comprising a GGGA motif as described herein, these ASOs might have been more efficacious.

The experiments described in this Example demonstrate that, in contrast to empirical screening, designing ASOs by targeting the fragments comprising a GGGA motif, as described in this Example, is much more likely to yield ASO sequences which are efficacious for inhibiting expression of a gene product.

Example 4

ASOs Which are Efficacious for Inhibiting Expression of Proteins Other than TNF-α

The inventors have used the strategy described herein to design ASOs which were efficacious for inhibiting expression of genes other than TNF-α. By way of example, a successful design of ASOs efficacious to inhibit expression of rat inducible nitric oxide synthase was described by Cao et al. (1998, Alcoholism Clin. Exp. Res. 22:108a).

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of making an antisense oligonucleotide for inhibiting expression of a gene in an animal, the method comprising
identifying an RNA molecule corresponding to the gene, wherein the RNA molecule comprises a GGGA motif; and
synthesizing an oligonucleotide complementary to at least a portion of the RNA molecule, the portion comprising the motif, wherein the portion is selected on the basis of the presence of the motif in the portion, whereby the oligonucleotide is efficacious for inhibiting the gene.

2. The method of claim 1, wherein at least a portion of [said] the oligonucleotide comprises a randomly-generated sequence.

3. The method of claim 1, wherein the gene is a human gene.

4. The method of claim 1, wherein the RNA molecule is the primary transcript of the gene.

5. The method of claim 1, wherein the gene encodes TNF-α.

6. The method of claim 1, wherein the oligonucleotide is at least 90% complementary to the portion.

7. The method of claim 1, wherein the oligonucleotide comprises from 14 to 30 nucleotide residues, and wherein at least 50% of the nucleotide residues of the oligonucleotide are complementary to the portion.

8. The method of claim 1, wherein the oligonucleotide comprises from 16 to 21 nucleotide residues and is completely complementary to the portion.

9. The method of claim 1, wherein the animal is a human.

10. The method of claim 1, wherein the portion is part of a region selected from the group consisting of regions I-XXI of the human TNF-α gene, and wherein the oligonucleotide comprises from 12 to 50 nucleotide residues and is complementary to a GGGA motif in the region.

11. The method of claim 1, wherein at least one linkage between the nucleotide residues of said oligonucleotide is a ph-osphorothioate linkage.

12. The method of claim 1, wherein the RNA molecule is an mRNA of the gene.

13. A method of making an antisense oligonucleotide for inhibiting expression of a gene in an animal, the method comprising
designing a nucleotide sequence that is complementary to a portion of an RNA molecule corresponding to the gene, the portion including a GGGA motif, wherein the portion is selected on the basis of the presence of the motif in the portion, and
synthesizing an oligonucleotide having the nucleotide sequence, whereby the oligonucleotide is an antisense oligonucleotide efficacious for inhibiting expression of the gene.

* * * * *